(12) United States Patent
Becker et al.

(10) Patent No.: US 10,280,261 B2
(45) Date of Patent: May 7, 2019

(54) RADIOOPAQUE, IODINE FUNCTIONALIZED PHENYLALANINE-BASED POLY(ESTER UREA)S

(71) Applicants: Matthew L. Becker, Stow, OH (US); Shan Li, Cuyahoga Falls, OH (US)

(72) Inventors: Matthew L. Becker, Stow, OH (US); Shan Li, Cuyahoga Falls, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 125 days.

(21) Appl. No.: 15/330,815

(22) PCT Filed: May 7, 2015

(86) PCT No.: PCT/US2015/029619
§ 371 (c)(1),
(2) Date: Nov. 7, 2016

(87) PCT Pub. No.: WO2015/171854
PCT Pub. Date: Nov. 12, 2015

(65) Prior Publication Data
US 2017/0081476 A1 Mar. 23, 2017

Related U.S. Application Data

(60) Provisional application No. 61/989,708, filed on May 7, 2014.

(51) Int. Cl.
*A61K 9/00* (2006.01)
*C08G 71/02* (2006.01)
(Continued)

(52) U.S. Cl.
CPC .............. *C08G 71/02* (2013.01); *A61L 27/18* (2013.01); *A61L 27/56* (2013.01)

(58) Field of Classification Search
CPC ...................................................... C08G 71/02
See application file for complete search history.

(56) References Cited

U.S. PATENT DOCUMENTS

5,705,333 A * 1/1998 Shah .................... C07K 14/003
435/375
7,649,022 B2 1/2010 Gomurashvili et al.
(Continued)

OTHER PUBLICATIONS

Jiayi Ju; Radiopaque, Iodine Functionalized, Phenylalanine-Based Poly(Ester urea)s; Article Biomacromolecules—Jan. 2015; 11 pages.
(Continued)

*Primary Examiner* — Paul W Dickinson
(74) *Attorney, Agent, or Firm* — Renner Kenner Greive Bobak Taylor & Weber

(57) ABSTRACT

In one or more embodiments, the present invention provides iodine-functionalized phenylalanine-based poly(ester urea)s (PEUs) (and related methods for their synthesis and use) that are metal free, degradable, radiopaque and suitable for use in surgical implants and other medical devices used within a patient. In one or more embodiment of the present invention 4-Iodo-L-phenylalanine and L-phenylalanine are separately reacted with 1,6-hexanediol to produce two monomers, bis-4-I-L-phenylalanine-1,6-hexanediol-diester (1-IPHE-6 monomer) and bis-L-phenylalanine-1,6-hexanediol-diester (1-PHE-6 monomer). It has been found that by varying the feed ratio of the 1-IPHE-6 and 1-PHE-6 monomers, the copolymer composition may be modulated to predictably create phenylalanine-based PEUs having a wide variation in thermal, mechanical and radiopacity properties. As most medical device procedures require placement verification via fluoroscopic imaging, materials that possess inherent X-ray contrast are valuable for a number of applications.

26 Claims, 13 Drawing Sheets

(51) Int. Cl.
   *A61L 27/18*   (2006.01)
   *A61L 27/56*   (2006.01)

(56)   References Cited

U.S. PATENT DOCUMENTS

| | | | |
|---|---|---|---|
| 2006/0036316 A1* | 2/2006 | Zeltinger | A61L 31/18 623/1.49 |
| 2009/0253809 A1* | 10/2009 | Gomurashvili | A61K 31/74 514/773 |
| 2010/0003268 A1 | 1/2010 | Samnick | |
| 2011/0022161 A1 | 1/2011 | Uhrich et al. | |

OTHER PUBLICATIONS

Jiayi Yu; Phenylalanine-Based Poly(ester urea); Synthesis, Characterization, and in vitro Degradation; Article in Macromolecules; Dec. 2013; 10 pages.

Yanyin Yang, et al.; X-Ray Imaging Optimization of 3D tissue engineering scaffolds via combinatorial fabrication methods; 17 pages.

ISA/US Commissioner for Patents; International Search Report; 2 pages.

\* cited by examiner

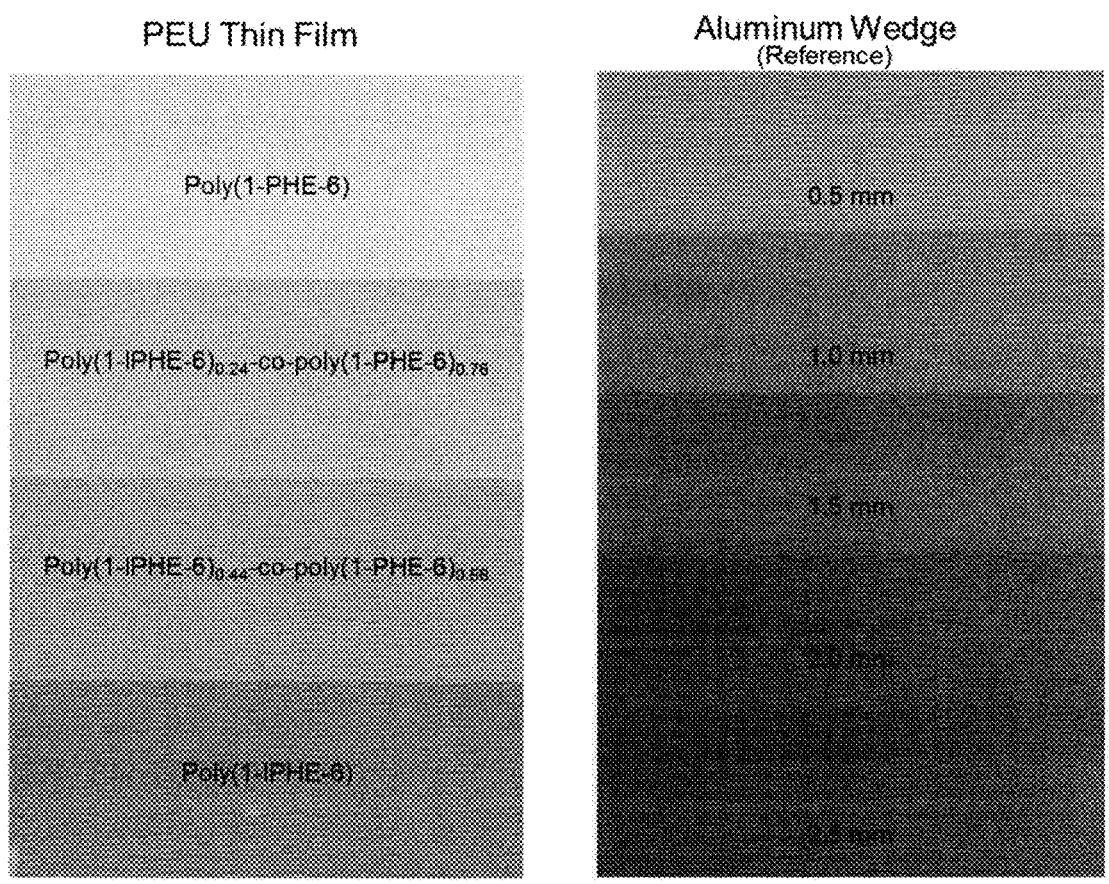

Poly(1-PHE-6) Scaffold

Poly(1-IPHE-6)₀.₂₄-co-poly(1-PHE-6)₀.₇₆ Scaffold

Poly(1-IPHE-6)₀.₄₄-co-poly(1-PHE-6)₀.₅₆ Scaffold (Poly(1-PHE-6)

(Poly(1-IPHE-6)0.24-co-poly(1-PHE-6)0.76

Poly(1-IPHE-6)0.44-co-poly(1-PHE-6)0.56

Poly(1-IPHE-6)₀.₁₂-co-poly(1-PHE-6)₀.₈₈     Poly(1-PHE-6)

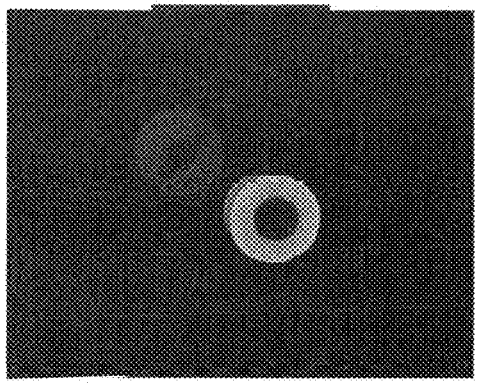
FIG. 7A
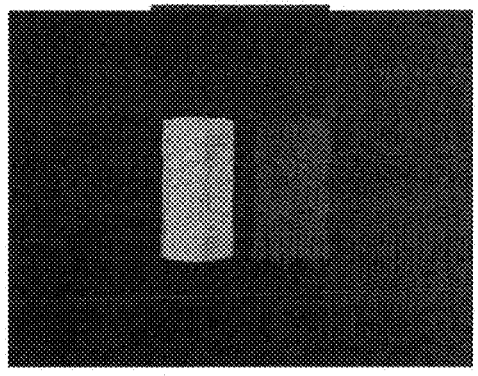
FIG. 7B
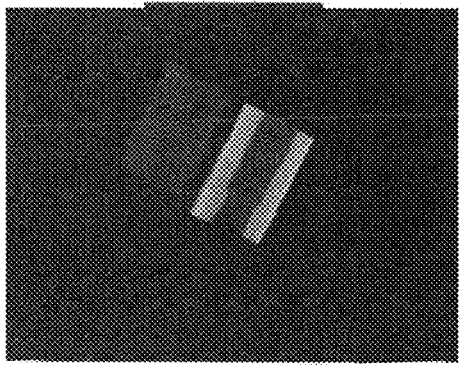
FIG. 7C
FIG. 7D
FIG. 8
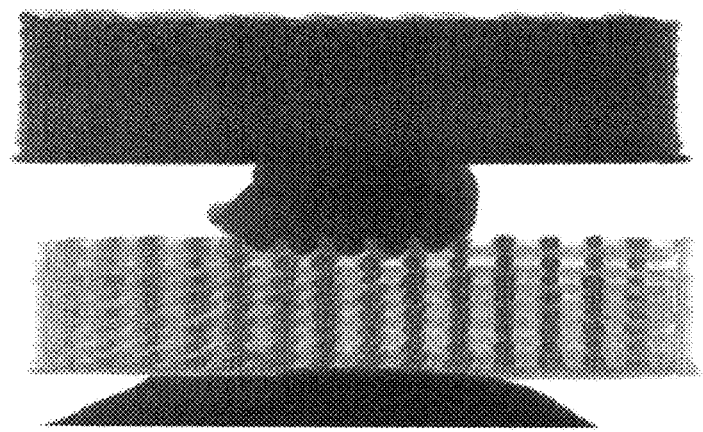
Poly(1-IPHE-6)$_{0.12}$-co-poly(1-PHE-6)$_{0.88}$
Poly(1-PHE-6)

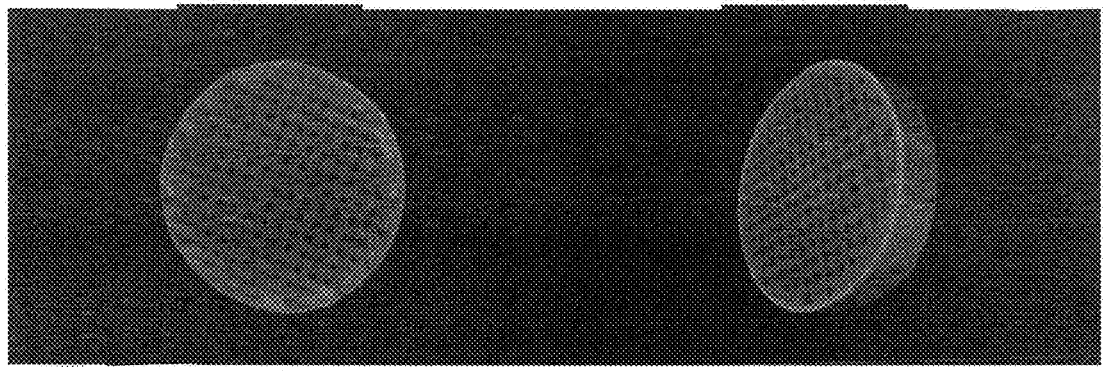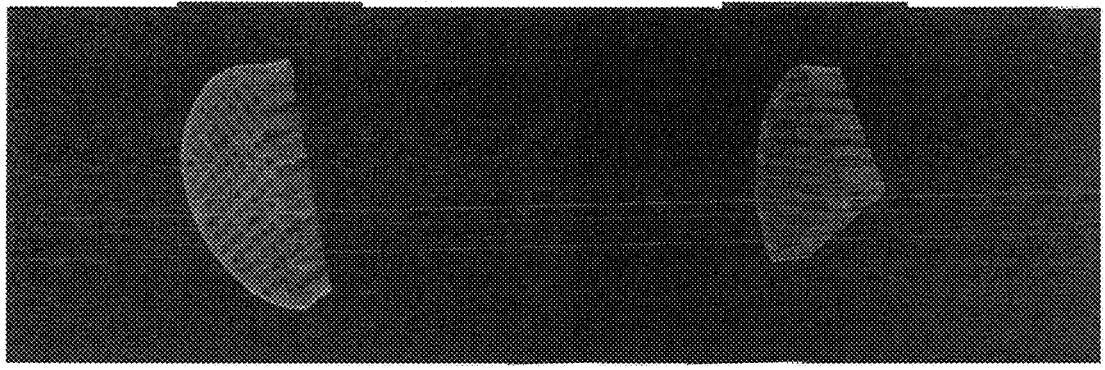

(a) Poly(1-IPHE-6)
(b) Poly(1-IPHE-6)$_{0.44}$-co-poly(1-PHE-6)$_{0.56}$
(c) Poly(1-IPHE-6)$_{0.24}$-co-poly(1-PHE-6)$_{0.76}$
(d) Poly(1-PHE-6)

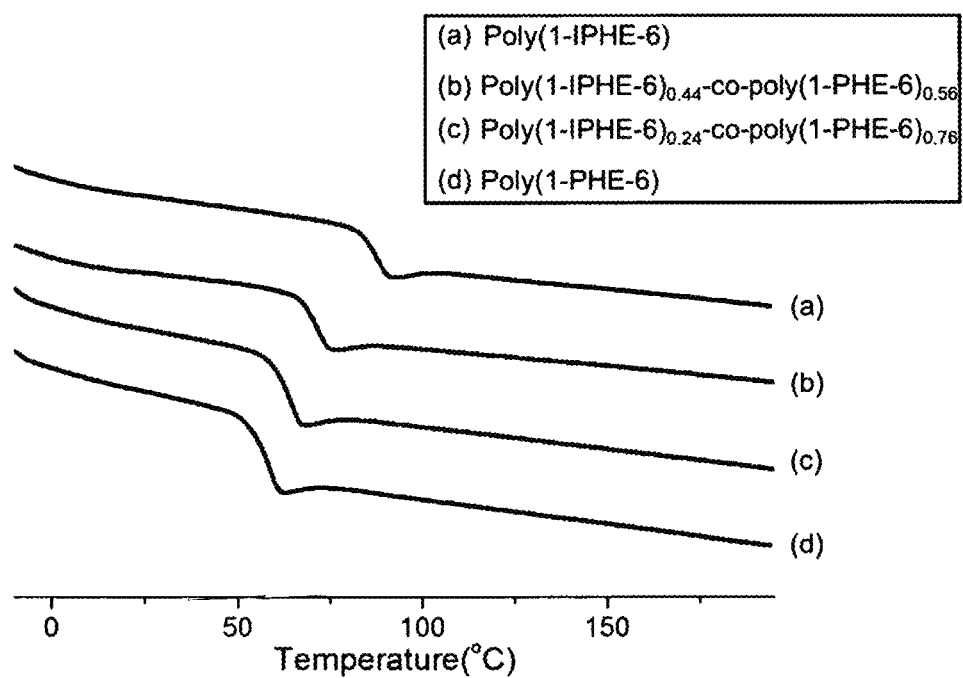
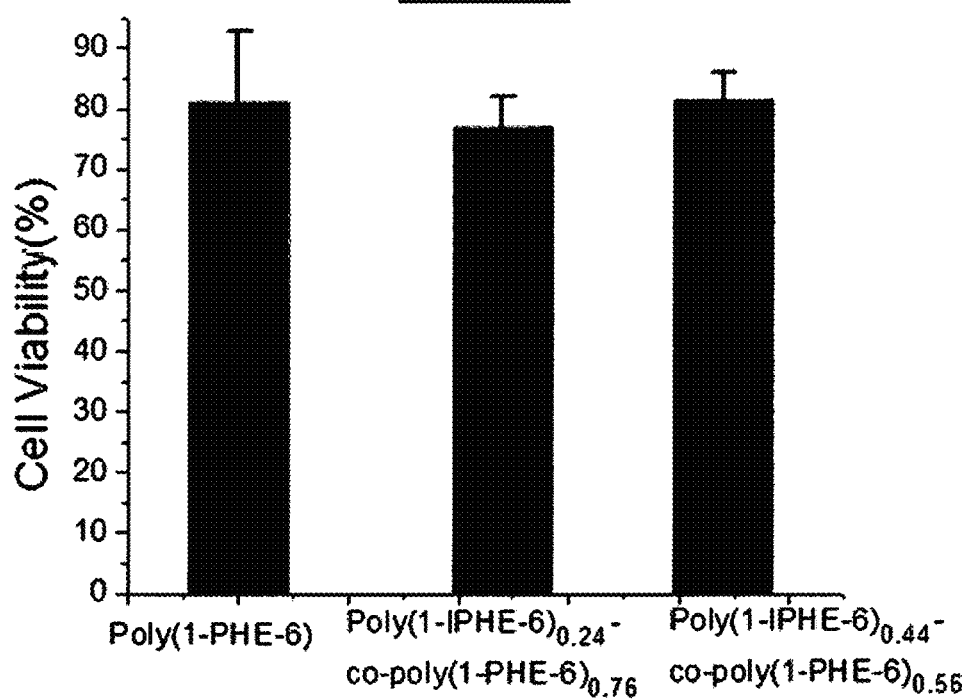

RADIOOPAQUE, IODINE FUNCTIONALIZED PHENYLALANINE-BASED POLY(ESTER UREA)S

CROSS REFERENCE TO RELATED APPLICATIONS

This application claims the benefit of International Patent Application No. PCT/US2015/029619 entitled "Radioopaque, Iodine Functionalized Phenylalanine-Based Poly(Ester Urea)s" filed May 7, 2016, and claiming the benefit of U.S. provisional patent application Ser. No. 61/989,708 entitled "Metal free, Degradable Radiopaque Poly(ester urea)s," filed May 7, 2014, both of which are incorporated herein by reference in their entirety.

FIELD OF THE INVENTION

One or more embodiments of the present invention relates to a radiopaque polymer for use in surgical implants and other medical devices used within a patient. In certain embodiments, the present related to metal free, degradable, radiopaque poly(ester urea) polymers for use in surgical implants and other medical devices used within a patient.

BACKGROUND OF THE INVENTION

Surgeons rely on fluoroscopic imaging to track the placement of medical devices and implants in patients. This is especially challenging, however, when the devices are polymeric. Conventional polymers are not easily detected using physiologically relevant X-ray radiography because their radiopacity is similar to that of human tissue as a result of the similar C, H, O and N elemental composition. Polymeric biomaterials with enhanced radiopacity have been extensively studied in recent years due to their potential applications in implantable orthopedic, prostheses and vascular devices that remain visible to X-ray after implantation. The ability of an element to attenuate X-rays is correlated with the atomic number of the element to the fourth power. Hence, heavy atoms, including iodine, have been utilized to impart radiopacity into polymers and enhance X-ray contrast.

Most enhancement strategies focus on two methods to modify the radiopacity of polymers. The first is to make radiopaque blends by incorporating radiopaque additives such as inorganic salts of heavy elements ($La_2O_3$, BaO, BaSO4, SrO, $ZrO_2$, $Ta_2O_5/SiO_2$, or $SrCO_3$), or organic compounds with heavy atoms (triphenyl bismuth, $I_4C_2B_{10}H_8$). The majority of commercial radiopaque polymeric medical implants currently available are prepared in this way because it is relatively easy to manufacture them using extrusion and molding, and the contrast can be controlled by adjusting the blending ratio. However, physical blending has been found to possess some significant drawbacks. It is difficult to achieve stable blend dispersions, and the limited compatibility of polymers with radiopaque additives can lead to contrast agent leakage, which can subsequently lead to a decrease in radiopacity and invoke unwanted biological responses and mechanical failures.

A second known method for enhancing contrast involves synthesizing polymers that possess covalently bonded heavy atoms. Monomers have been prepared containing covalently bonded iodine (4-IEMA) and terpolymerized 4-IEMA with 2-hydroxyethyl methacrylate (HEMA) and methyl methacrylate (MMA). Electron spectroscopy for chemical analysis (ESCA) demonstrated the stability of this iodinated polymer. In these methods, iodine is incorporated into poly(ether urethane) in a two-step condensation polymerization by using an iodine-containing diol. This iodinated poly(ether urethane) has high radiopacity, good thermal stability and was not cytotoxic. In addition, the preparation of iodinated and/or brominated derivatives of dihydroxy monomers and polymers with different structures have been demonstrated and these polymers have been found to be degradable and tissue-compatible. Iodine-modified poly(desaminotyrosyl-tyrosine ethyl ester carbonate) ($pI_2DTEc$) polymers synthesized using a monomer containing iodine atoms in the 3,5 position of the aromatic rings of tyrosine have also been reported.

Unfortunately, however, incorporation of iodine atoms into these polymers has been found to have a distinct influence on the mechanical and protein adsorption properties of the resulting polymers. Combinatorial methods have been used to determine the minimal amount of iodinated polymer needed to have sufficient X-ray contrast under a variety of translationally relevant imaging conditions. Such chemical modification introduces radiopacity intrinsically into polymers, but generates polymers lacking the necessary mechanical strength.

Amino acid-based poly(ester urea)s (PEUs) are finding use in a number of regenerative medicine applications due to their inherent synthetic flexibility, which results in tunable mechanical and degradation properties. The resulting polymers are semi-crystalline depending on the amino acid precursors, and the hydrogen bonding in the urea groups imparts the polymers with strong mechanical properties. The ester and urea bonds allow for both hydrolytic and enzymatic degradation. The final degradation byproducts are amino acids, small diol segments and $CO_2$, which can be readily metabolized and/or removed by the body. Moreover, unlike the acidic degradation byproducts of polyesters, the carboxyl group in PEU is buffered by the urea linkages at each repeat unit. It is believed, therefore, that the lack of inflammation found in vivo with PEU polymers is due, at least in part, to the absence of localized acidification during and after PEU degradation. Further, histological analysis of PEUs has shown that they are nontoxic and are therefore excellent candidates for tissue engineering constructs. Significantly, PEUs are synthetically flexible in that there are 20 kinds of naturally occurring amino acids and a number of non-natural amino acids derivatives have been successfully used in a number of applications. These amino acids, along with the various diols commercially available, permit the synthesis of PEUs having vastly different properties.

PEUs can also be chemically modified with bioactive groups to initiate specific responses both in vitro and in vivo. Growth factors and peptides, including osteogenic growth peptide (OGP), have been used to crosslink PEUs in order to increase the mechanical properties and bioactivity of the resulting materials. (See, Stakleff, K. S.; Lin, F.; Callahan, L. A. S.; Wade, M. B.; Esterle, A.; Miller, J.; Graham, M.; Becker, M. L. *Acta Biomater.* 2013, 9, 5132-5142, the disclosure of which is incorporated herein by reference in its entirety.) Chemical modification of PEUs with pendant clickable groups in order to fabricate functional nanofibers has also been reported. (See, Lin, F.; Yu, J. Y.; Tang, W.; Zheng, J. K.; Xie, S. B.; Becker, M. L. *Macromolecules* 2013, 46, 9515-9525, the disclosure of which is incorporated herein by reference in its entirety.)

Unfortunately, however, these PEU materials also lack radiopacity. Therefore enhancing X-ray contrast is necessary to increase the translational potential of these materials. Contrast enables use of X-ray fluoroscopy to show the clinician the precise location of the devices in vivo effectively and efficiently. The level of contrast needed varies with a number of factors including X-ray flux, tissue coverage and location relative to bone and other internal structures. Minimizing chemical modifications can reduce the variance in the physical-chemical properties. As such, there is a fine balance between ensuring sufficient contrast in a material while minimizing physical property changes to the polymer.

Accordingly, what is needed in the art is an amino acid based poly(ester urea) polymer (and related methods of making and use) that is metal free, degradable, radiopaque and suitable for use in surgical implants and other medical devices used within the body of a patient.

SUMMARY OF THE INVENTION

One or more embodiments of the present invention provide iodine-functionalized phenylalanine-based poly(ester urea)s (PEUs) (and related method of making and use) that are metal free, degradable, radiopaque and suitable for use in surgical implants and other medical devices used within a patient. In one or more embodiment of the present invention 4-Iodo-L-phenylalanine and L-phenylalanine are separately reacted with 1,6-hexanediol to produce two monomers, bis-4-I-L-phenylalanine-1,6-hexanediol-diester (1-IPHE-6 monomer) and bis-L-phenylalanine-1,6-hexanediol-diester (1-PHE-6 monomer). It has been found that by varying the feed ratio of the 1-IPHE-6 and 1-PHE-6 monomers, the copolymer composition may be modulated to predictably create phenylalanine-based PEUs having a wide variation in thermal, mechanical and radiopacity properties. Micro-computed tomography (μ-CT) projections demonstrate that increasing iodine content in these PEUs results in greater X-ray contrast. As most medical device procedures require placement verification via fluoroscopic imaging, materials that possess inherent X-ray contrast are valuable for a number of applications.

In a first aspect, the present invention is directed to a radiopaque poly(ester urea) polymer comprising two or more amino acid-based monomer segments containing at least one amino acid residue functionalized to include a radiopaque atom. In some embodiments, the radiopaque atom is selected from the group consisting of iodine, boron, and combinations thereof. In one or more embodiments, the radiopaque poly(ester urea) polymer of the present invention includes any one or more of the above referenced embodiments of the first aspect of the present invention wherein, the radiopaque atom is iodine. In one or more embodiments, the radiopaque poly(ester urea) polymer of the present invention includes any one or more of the above referenced embodiments of the first aspect of the present invention wherein, the amino acid residue is an L-phenylalanine residue.

In one or more embodiments, the radiopaque poly(ester urea) polymer of the present invention includes any one or more of the above referenced embodiments of the first aspect of the present invention having the formula:

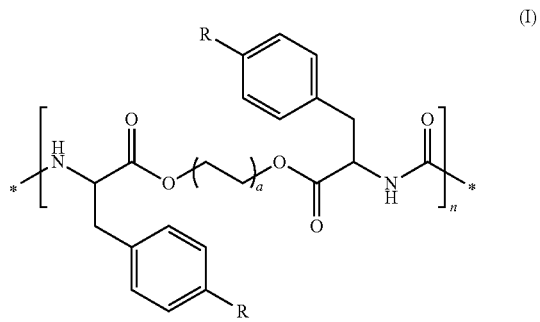

(I)

wherein R is I or H, a is an integer from 2 to 20, and n is an integer from 10 to 1000.

In a second aspect, the present invention is directed to a radiopaque poly(ester urea) polymer comprising: one or more first amino acid-based monomer segments, wherein the first amino acid-based monomer segments further comprise two or more iodine functionalized amino acid residues separated by from about 2 to about 20 carbon atoms; and one or more second amino acid-based monomer segments, wherein the second amino acid-based monomer segments further comprise two or more amino acid residues separated by from about 2 to about 20 carbon atoms.

In one or more embodiments, the present invention is directed to the radiopaque poly(ester urea) polymer of the second aspect of the present invention wherein the two or more iodine functionalized amino acid residues are iodine functionalized L-phenylalanine residues. In one or more embodiments, the radiopaque poly(ester urea) polymer of the present invention includes any one or more of the above referenced embodiments of the second aspect of the present invention wherein the two or more amino acid residues of the second amino acid-based monomer segments are residues of alanine (ala-A), arginine (arg-R), asparagine (asn-N), aspartic acid (asp-D), cysteine (cys-C), glutamine (gin-Q), glutamic acid (glu-E), glycine (gly-G), histidine (his-H), isoleucine (ile-I), leucine (leu-L), lysine (lys-K), methionine (met-M), phenylalanine (phe-F), serine (ser-S), threonine (thr-T), tryptophan (trp-W), tyrosine (tyr-Y), or valine (val-V).

In one or more embodiments, the radiopaque poly(ester urea) polymer of the present invention includes any one or more of the above referenced embodiments of the second aspect of the present invention wherein the two or more iodine functionalized amino acid residues comprise 4-iodo-L-phenylalanine. In one or more embodiments, the radiopaque poly(ester urea) polymer of the present invention includes any one or more of the above referenced embodiments of the second aspect of the present invention wherein the one or more first amino acid-based monomer segments comprise the residue of bis-4-I-L-phenylalanine-1,6-hexanediol-diester.

In one or more embodiments, the radiopaque poly(ester urea) polymer of the present invention includes any one or more of the above referenced embodiments of the second aspect of the present invention wherein the two or more iodine functionalized amino acid residues are separated by from about 2 to about 20 carbon atoms. In one or more embodiments, the radiopaque poly(ester urea) polymer of the present invention includes any one or more of the above referenced embodiments of the second aspect of the present invention wherein the two or more iodine functionalized amino acid residues are separated by six carbon atoms. In one or more embodiments, the radiopaque poly(ester urea) polymer of the present invention includes any one or more of the above referenced embodiments of the second aspect of the present invention wherein the two or more amino acid residues of the second amino acid-based monomer segments are separated by from about 2 to about 20 carbon atoms. In one or more embodiments, the radiopaque poly(ester urea) polymer of the present invention includes any one or more of the above referenced embodiments of the second aspect of the present invention wherein two or more amino acid residues of the second amino acid-based monomer segments are separated by six carbon atoms.

In one or more embodiments, the radiopaque poly(ester urea) polymer of the present invention includes any one or more of the above referenced embodiments of the second aspect of the present invention having the formula:

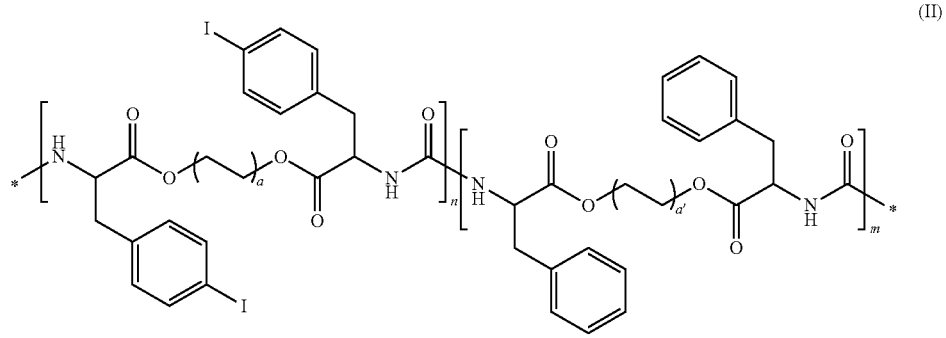

(II)

wherein a and a' are each integers from 2 to 20; n is a mole percentage from about 1 to about 100; and m is a mole percentage from about 0 to about 99. In one or more embodiments, the radiopaque poly(ester urea) polymer of the present invention includes any one or more of the above referenced embodiments of the second aspect of the present invention wherein the first amino acid-based monomer segments comprise from 1% to 100% of the radiopaque poly(ester urea) polymer.

In a third aspect, the present invention is directed to a method for making a radiopaque poly(ester urea) polymer comprising: dissolving L-phenylalanine, a linear or branched polyol having from about 2 to about 60 carbon atoms, and an acid in a suitable solvent; refluxing the resulting solution of at a temperature of from about 110° C. to about 114° C. for from 24 hours to 72 hours to form the acid salt of a first amino acid-based monomer having two or more L-phenylalanine residues separated by from about 2 to about 20 carbon atoms; dissolving L-phenylalanine functionalized with a radiopaque moiety, a linear or branched polyol having from 2 to about 60 carbon atoms, and an acid in a suitable solvent; refluxing the resulting mixture at a temperature of from about 110° C. to about 114° C. for from 24 hours to 72 hours to form the acid salt of a second amino acid-based monomer having two or more iodine functionalized L-phenylalanine residues separated by from about 2 to about 20 carbon atoms; dissolving the acid salt of the first amino acid-based monomer, the acid salt of the second amino acid based monomer, and an organic water soluble base in distilled water; cooling the mixture to a temperature of from about −10° C. to about 2° C.; dissolving an additional quantity of an organic water soluble base in distilled water and adding it to the mixture; dissolving a first fraction of triphosgene in distilled chloroform and adding it to the mixture; and dissolving a second fraction of triphosgene in distilled chloroform and adding it dropwise to the mixture over a period of from about 5 minutes to about 72 hours to form a radiopaque poly(ester urea) polymer.

In one or more embodiments, the present invention is directed to the method for making the radiopaque poly(ester urea) polymer of the third aspect of the present invention wherein the acid is p-toluene sulfonic acid monohydrate. In one or more embodiments, the method for making a radiopaque poly(ester urea) polymer of the present invention includes any one or more of the above referenced embodiments of the third aspect of the present invention wherein the organic water soluble base is sodium carbonate. In one or more embodiments, the method for making a radiopaque poly(ester urea) polymer of the present invention includes any one or more of the above referenced embodiments of the third aspect of the present invention wherein the radiopaque moiety is iodine.

In one or more embodiments, the method for making a radiopaque poly(ester urea) polymer of the present invention includes any one or more of the above referenced embodiments of the third aspect of the present invention further comprising: collecting and purifying the radiopaque poly(ester urea) polymer by transferring the mixture to a separatory funnel, thereby forming a aqueous layer and a organic layer containing the radiopaque poly(ester urea) polymer; adding the organic layer dropwise into boiling water thereby causing the radiopaque poly(ester urea) polymer to precipitate; and collecting the radiopaque poly(ester urea) polymer by filtration, and drying.

In one or more embodiments, the method for making a radiopaque poly(ester urea) polymer of the present invention includes any one or more of the above referenced embodiments of the third aspect of the present invention wherein the second amino acid based monomer is from about 1% to about 99%. In one or more embodiments, the method for making a radiopaque poly(ester urea) polymer of the present invention includes any one or more of the above referenced embodiments of the third aspect of the present invention wherein the molar ratio of the acid salt of the first amino acid-based monomer to the acid salt of the second amino acid based monomer is 1% to 99%.

In a fourth aspect, the present invention is directed to a medical device comprising the radiopaque poly(ester urea)

polymer of the first or second aspect of the invention. In one or more embodiments, the present invention is directed to the medical device of the fourth aspect of the present invention wherein the medical device comprises a tissue scaffold, a 3D printed material, drug eluting scaffold, thin film or coating. In one or more embodiments, the medical device of the present invention includes any one or more of the above referenced embodiments of the fourth aspect of the present invention wherein the medical device as formed using extrusion, three-dimensional (3D) printing, or injection molding.

BRIEF DESCRIPTION OF THE DRAWINGS

For a more complete understanding of the features and advantages of the present invention, reference is now made to the detailed description of the invention along with the accompanying figures in which:

FIG. 2 are Micro-CT images of PEU films according to embodiments of the present invention with different iodine contents and an aluminum wedge 0.5-2.5 mm in 0.5 mm steps, which was used as a reference. These images demonstrate that the radiopacity of PEUs increased with increasing iodine content. As can be seen, the poly(1-IPHE-6) film has comparable radio contrast to that of the aluminum reference with a thickness of 1 mm, the poly(1-IPHE-6)$_{0.4}$-co-poly(1-PHE-6)$_{0.56}$ film has comparable radio contrast as that of the aluminum reference with a thickness of 0.5 mm, and the radiopacity of poly(1-IPHE-6)$_{0.24}$-co-poly(1-PHE-6)$_{0.76}$ film is lower than that of the 0.5 mm thick aluminum reference, but is much higher than that of the poly(1-PHE-6) film.

FIG. 3A is an image of reconstruction slices of Micro-CT 3D scanning of porous scaffolds made with poly(1-PHE-6). FIG. 3B is an image of reconstruction slices of Micro-CT 3D scanning of porous scaffolds made with Poly(1-IPHE-6)$_{0.24}$-co-poly(1-PHE-6)$_{0.76}$. FIG. 3C is an image of reconstruction slices of Micro-CT 3D scanning of porous scaffolds made with poly(1-IPHE-6)$_{0.44}$-co-poly(1-PHE-6)$_{0.56}$. The images show the cross-section of the scaffold throughout the sample. It is difficult to see the poly(1-PHE-6) scaffold (FIG. 3A) structure because of the poor radiopacity. Poly(1-IPHE-6)$_{0.24}$-co-poly(1-PHE-6)$_{0.76}$ (FIG. 3B) and poly(1-IPHE-6)$_{0.44}$-co-poly(1-PHE-6)$_{0.56}$ (FIG. 3C) show the internal structure (pore size, pore type and interconnectivity) of the scaffolds. The porosity of poly(1-PHE-6) (FIG. 3A), (poly(1-IPHE-6)$_{0.24}$-co-poly(1-PHE-6)$_{0.76}$ (FIG. 3B) and poly(1-IPHE-6)$_{0.44}$-co-poly(1-PHE-6)$_{0.56}$) (FIG. 3C) scaffolds were calculated to be (90±1.6)%, (85±0.4)% and (88±0.5)%, respectively.

FIG. 4A is an image of reconstruction slices of Micro-CT 3D scanning of porous scaffolds made with poly(1-PHE-6). FIG. 4B is an image of reconstruction slices of Micro-CT 3D scanning of porous scaffolds made with Poly(1-IPHE-6)$_{0.24}$-co-poly(1-PHE-6)$_{0.76}$. FIG. 4C is an image of reconstruction slices of Micro-CT 3D scanning of porous scaffolds made with poly(1-IPHE-6)$_{0.44}$-co-poly(1-PHE-6)$_{0.56}$. The images show the cross-section of the scaffold throughout the sample. It is difficult to see the poly(1-PHE-6) scaffold (FIG. 4A) structure because of the poor radiopacity. Poly(1-IPHE-6)$_{0.24}$-co-poly(1-PHE-6)$_{0.76}$ (FIG. 4B) and poly(1-IPHE-6)$_{0.44}$-co-poly(1-PHE-6)$_{0.56}$ (FIG. 4C) show the internal structure (pore size, pore type and interconnectivity) of the scaffolds.

FIGS. 7A-D are 3D reconstruction images showing a top view (FIG. 7A), side view (FIG. 7B), cross sectional side view (FIG. 7C), and cross sectional end view (FIG. 7D) of a poly(1-IPHE-6)$_{0.12}$-co-poly(1-PHE-6)$_{0.88}$ scaffold and a poly(1-PHE-6) scaffold.

FIG. 8 is a μ-CT shadow projection of poly(1-IPHE-6)$_{0.12}$-co-poly(1-PHE-6)$_{0.88}$ (Dark) and poly(1-PHE-6) (Gray) orthogonally knitted porous scaffolds.

FIG. 11A-D (g): are 3D reconstruction images showing a top view (FIG. 11A), elevated view (FIG. 11B), half sectional view (FIG. 11C), and quarter sectional view (FIG. 11D) of a of poly(1-IPHE-6)$_{0.12}$-co-poly(1-PHE-6)$_{0.88}$ orthogonally knitted porous scaffold.

PHE-6) in the copolymer) (poly(1-IPHE-6)$_{0.24}$-co-poly(1-PHE-6)$_{0.76}$); and spectra (d) is of a homopolymer of the 1-PHE-6 monomer (poly(1-PHE-6), possessing proton resonances characteristic of the benzyl group, 7.1 to 7.3 ppm.

Figure 13:
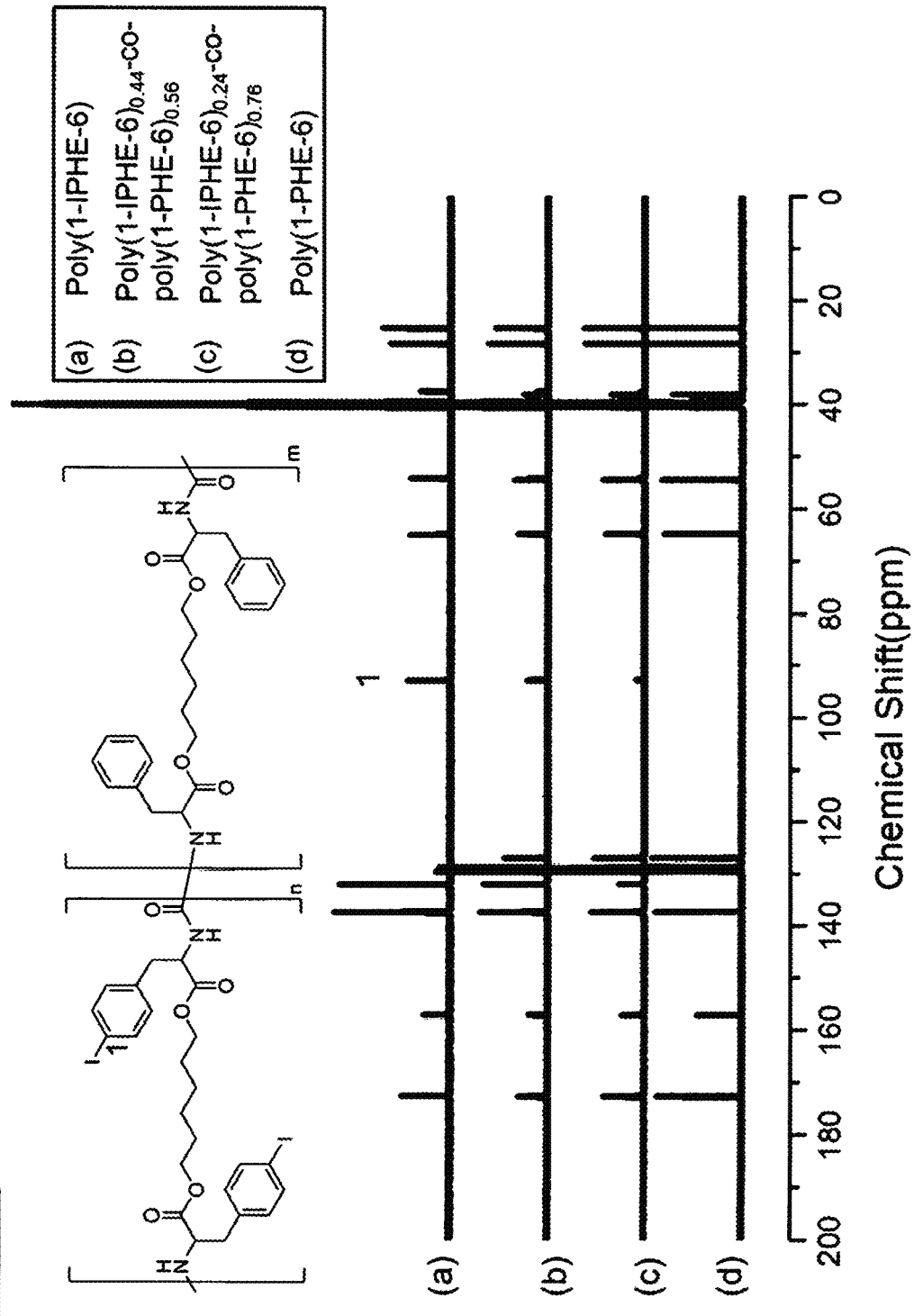

FIG. 13 is a schematic comparing $^{13}$CNMR (DMSO-d$_6$) spectra of: (a) iodinated phenylalanine-based poly(1-IPHE-6); (b) copolymer of 44% poly(1-IPHE-6) and 56% poly(1-PHE-6); (c) copolymer of 24% poly(1-IPHE-6) and 76% poly(1-PHE-6); (d) phenylalanine-based poly(1-PHE-6). In the benzyl ring, substitution of one hydrogen atom with an iodine atom results in a shift from around 130 ppm to 93 ppm. With the increase in iodine content, the intensity of the characteristic C-I peak at 93 ppm increases.

Figure 14:
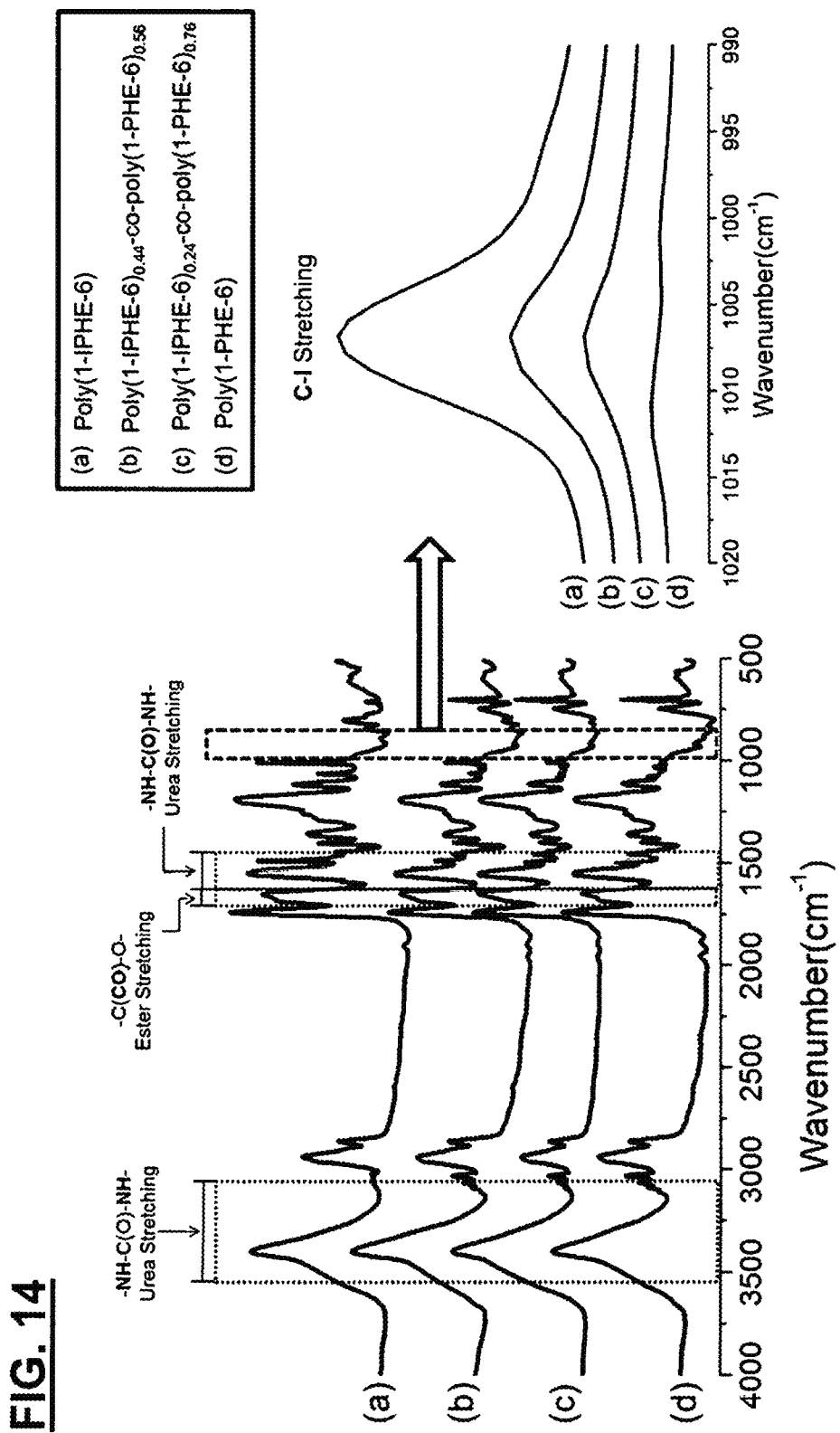

FIG. 14 is a comparison of FT-IR spectra of PEUs according to one or more embodiments of the present invention, wherein spectra (a) is of poly(1-IPHE-6); spectra (b) is of poly(1-IPHE-6)$_{0.44}$-co-poly(1-PHE-6)$_{0.56}$; (c) is of poly(1-IPHE-6)$_{0.24}$-co-poly(1-PHE-6)$_{0.76}$; and (d) phenylalanine-based poly(1-PHE-6), showing the urea (—NH—C(O)—NH—) stretching, ester (—C(CO)—O—) stretching, and C-I stretching regions. All four spectra show the characteristic ester and urea peaks. The spectra for the iodinated polymers, (spectra (a), (b) and (c)), show the characteristic C-I stretching signal at 1007 cm$^{-1}$, the amplitude of which increased with greater iodine content.

FIG. 15 is a schematic comparing the Differential Scanning calorimetry (DSC) curves of PEUs according to embodiments of the present invention at a scanning rate of 20° C./min. $_{The}$ second cycle was used to determine Tg after the removal of any thermal history in the first cycle.

FIG. 16 is a graph showing the results of cell viability rests on PEU films according to embodiments of the present invention having different iodine contents. These results show no significant difference in cell viability.

Figure 17:
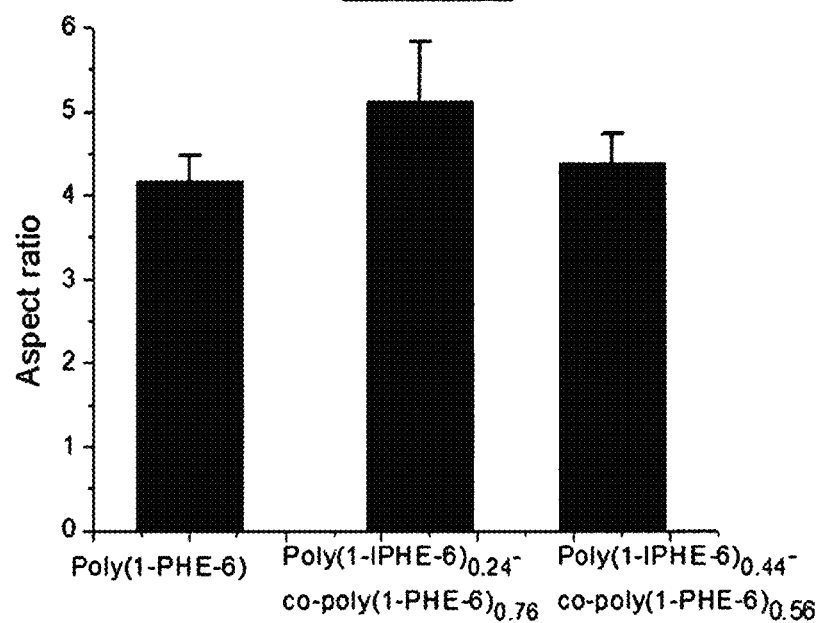

FIG. 17 is a graph showing the aspect ratio results from MC3T3 cell spreading assays done on PEU films according to embodiments of the present invention having different iodine contents (n=3). 20 images were used for quantification of cell aspect ratio for each sample.

Figure 18:
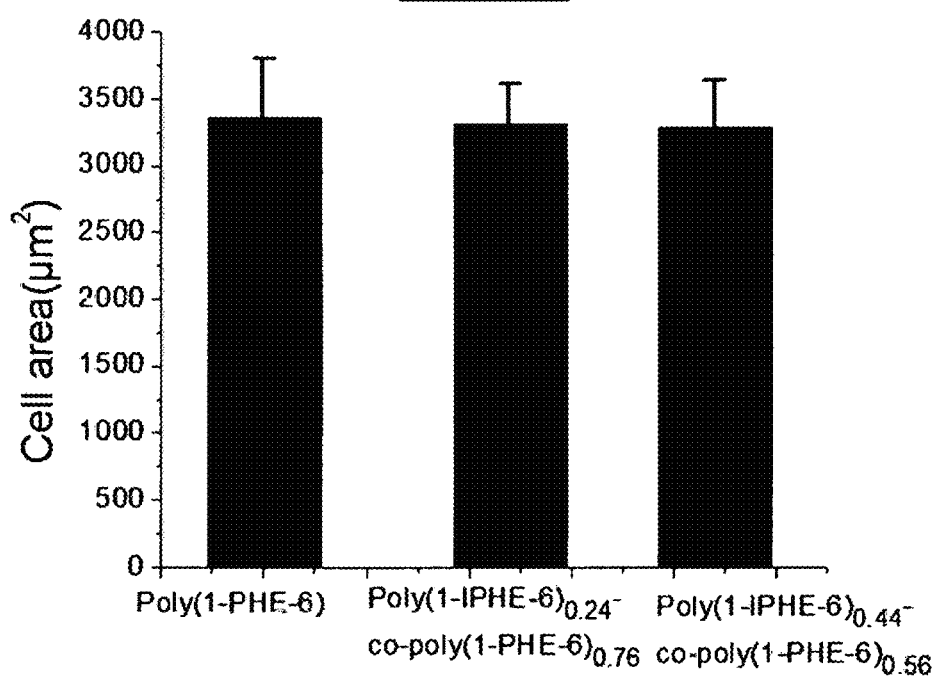

FIG. 18 is a graph showing the cell area results from MC3T3 cell spreading assays done on PEU films according to embodiments of the present invention having different iodine contents (n=3). 20 images were used for quantification of cell area for each sample.

DETAILED DESCRIPTION OF THE ILLUSTRATIVE EMBODIMENTS

In one or more embodiments, the present invention provides iodine-functionalized phenylalanine-based poly(ester urea)s (PEUs) (and related methods for their synthesis and use) that are metal free, degradable, radiopaque and suitable for use in surgical implants and other medical devices used within a patient. As used herein, the term "radiopacity" refers to the ability of an object or material to block one or another form of radiation, such as X-rays, rather than allow it to pass through. In more practical terms, the radiopacity of an object or material refers to its ability to be seen on x-rays or other similar scans and an object of material may be said to be "radiopaque" if it blocks enough radiation to create a clinically useful result.

In one or more embodiment of the present invention 4-Iodo-L-phenylalanine and L-phenylalanine are separately reacted with 1,6-hexanediol to produce two monomers, bis-4-I-L-phenylalanine-1,6-hexanediol-diester (1-IPHE-6 monomer) and bis-L-phenylalanine-1,6-hexanediol-diester (1-PHE-6 monomer). It has been found that by varying the feed ratio of the 1-IPHE-6 and 1-PHE-6 monomers, the copolymer composition may be modulated to predictably create phenylalanine-based PEUs having a wide variation in thermal, mechanical and radiopacity properties. Micro-computed tomography (μ-CT) projections demonstrate that increasing iodine content in these PEUs results in greater X-ray contrast. As most medical device procedures require placement verification via fluoroscopic imaging, materials that possess inherent X-ray contrast are valuable for a number of applications.

In a first aspect, embodiments of the present invention are directed to iodine-functionalized phenylalanine-based poly(ester urea)s (PEUs) that are metal free, degradable, radiopaque and suitable for use in surgical implants and other medical devices used within a patient. In one or more embodiment, the PEUs of the present invention may be a homopolymer having the following formula:

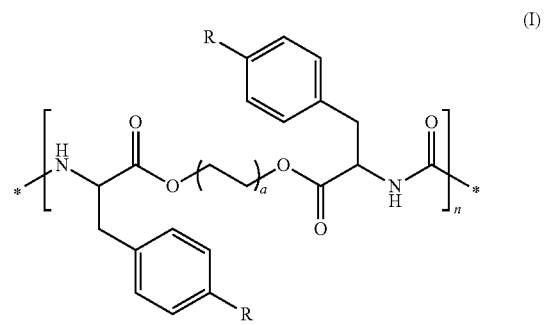

wherein R is H or a large radiopaque atom such as iodine or boron, a is an integer from about 2 to about 20, and n is an integer from about 10 to about 1000. In some of these embodiments, a is an integer from about 2 to about 18. In some of these embodiments, a is an integer from about 2 to about 15. In some of these embodiments, a is an integer from about 10 to about 20. In some of these embodiments, a is an integer from about 2 to about 10. In some of these embodiments, n is an integer from about 10 to about 700. In some of these embodiments, n is an integer from about 10 to about 400. In some of these embodiments, n is an integer from about 10 to about 150. In some of these embodiments, n is an integer from about 10 to about 50. In some of these embodiments, R is I, a is 3, and n is an integer from about 100 to about 1000.

It should be noted, however, that for the PEU to be radiopaque, at least some of the segments of the PEU must contain a large radiopaque atom such as iodine or boron (e.g., R is I or B). While it should be appreciated that the large radiopaque atom incorporated into the PEUs of the present invention are not limited to iodine, iodine has been found to be well suited to these applications because it is naturally occurring in the body and non-toxic. Accordingly, polymer segments wherein R is a large radiopaque atom, such as iodine or boron will be referred to herein as "IPEU segments". In some embodiments and as discussed in more detail below, the IPEU segments are the residue of the iodine functionalized L-phenylalanine monomers segments that were used to form the polymer. While it is expected that both R groups in an IPEU segment will ordinarily be the same, there are embodiments within the scope of the present invention where the R groups in an IPEU segment are different. In some embodiments, the two R groups in an IPEU segment may be different radiopaque atoms. In some embodiments, one R group in an IPEU segment may be a large radiopaque atoms and the other R group may be hydrogen.

While, as set forth above, the radiopaque PEUs of the present invention may comprise homopolymerized IPEU segments, it has been found that the addition of iodine can affect the mechanical properties of the PEU. Initially, incorporation of iodine makes the normally brittle PEUs more ductile. However, it has been found that with increasing iodine content, the PEUs again become brittle. While not wishing to be bound by theory, it is believed that the introduction of the relatively large iodine atoms to these PEUs initially breaks up the chain space of the polymer, reducing the hydrogen bonding and increasing the elasticity of the polymer. As the iodine content increases, however, there reaches a point at which the polymer will become increasingly brittle. The precise point at which the iodine atoms start to increase the brittleness of the polymer will depend on a variety of factors including the molecular weight of the PEU being used. Poly(1-IPHE-6) homopolymer, for example, was too brittle to be measured by Dynamic Mechanical Analysis (DMA).

In these homopolymer embodiments, the amount of iodine, and therefore the opacity and brittleness of the PEUs of embodiments of the present invention, may be regulated by controlling the ratio of iodine functionalized amino acids (radiopaque) to non-iodine functionalized amino acids (not radiopaque) used to make the monomer.

percent IPEU segments. In some embodiments, the PEUs of the present invention may comprise from about 1 to about 60 mole percent IPEU segments. In some embodiments, the PEUs of the present invention may comprise from about 1 to about 40 mole percent IPEU segments. In some embodiments, the PEUs of the present invention may comprise from about 1 to about 20 mole percent IPEU segments. In some embodiments, the PEUs of the present invention may comprise from about 20 to about 80 mole percent IPEU segments.

In some embodiments, the PEUs of the present invention may comprise from about 0 to about 99 mole percent non-functionalized PEU segments. In some embodiments, the PEUs of the present invention may comprise from about 0 to about 80 mole percent non-functionalized PEU segments. In some embodiments, the PEUs of the present invention may comprise from about 0 to about 60 mole percent non-functionalized PEU segments. In some embodiments, the PEUs of the present invention may comprise from about 0 to about 40 mole percent non-functionalized PEU segments. In some embodiments, the PEUs of the present invention may comprise from about 0 to about 20 mole percent non-functionalized PEU segments. In some embodiments, the PEUs of the present invention may comprise from about 20 to about 80 mole percent non-functionalized PEU segments.

In some embodiments, the PEUs of the present invention may have the following formula:

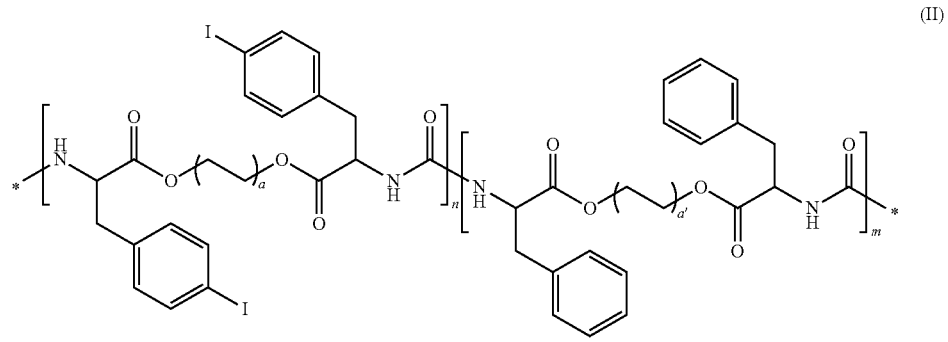

(II)

In order to regulate the amount of iodine or other relatively large radiopaque atom, PEUs according to one or more embodiment of the present invention may be a copolymer comprising both IPEU segments and non-functionalized PEU segments having the same general formula (I) as the IPEU segments described above wherein R=H (for all of these segments) and a is an integer from about 2 to about 20 (referred to herein as "non-functionalized PEU segments" or just "PEU segments"). In some embodiments (and as discussed in more detail below), the non-functionalized PEU segments are the residue of the L-phenylalanine monomers used to form the polymer. In some of these embodiments, a is an integer from about 2 to about 17. In some of these embodiments, a is an integer from about 2 to about 13. In some of these embodiments, a is an integer from about 10 to about 20. In some of these embodiments, a is an integer from about 2 to about 10. In some of these embodiments, a is 6.

In some embodiments, the PEUs of the present invention may comprise from about 1 to about 100 mole percent IPEU segments. In some embodiments, the PEUs of the present invention may comprise from about 1 to about 80 mole wherein a and a' are integers from 2 to 20, n is a mole percentage of IPEU segments from about 1 to about 100 and m is a mole percentage of non-functionalized PEU segments from about 0 to about 99. In some of these embodiments, a and a' are integers from 2 to 17. In some of these embodiments, a and a' are integers from 2 to 13. In some of these embodiments, a and a' are integers from 2 to 10. In some of these embodiments, a and a' are integers from 10 to 20. In some of these embodiments, a and a' are integers from 6 to 10.

In some of these embodiments, n is a mole percent of from about 1 to about 80. In some of these embodiments, n is a mole percent of from about 1 to about 60. In some of these embodiments, n is a mole percent of from about 1 to about 40. In some of these embodiments, n is a mole percent of from about 1 to about 20. In some of these embodiments, n is a mole percent of from about 20 to about 80. In some of these embodiments, m is a mole percent of from about 0 to about 99. In some of these embodiments, m is a mole percent of from about 0 to about 80. In some of these embodiments, m is a mole percent of from about 0 to about 60. In some of these embodiments, m is a mole percent of from about 0 to about 40. In some of these embodiments, m is a mole percent of from about 0 to about 20. In some of these embodiments, m is a mole percent of from about 20 to about 80.

In some embodiments, the PEUs of the present invention may have the following formula:

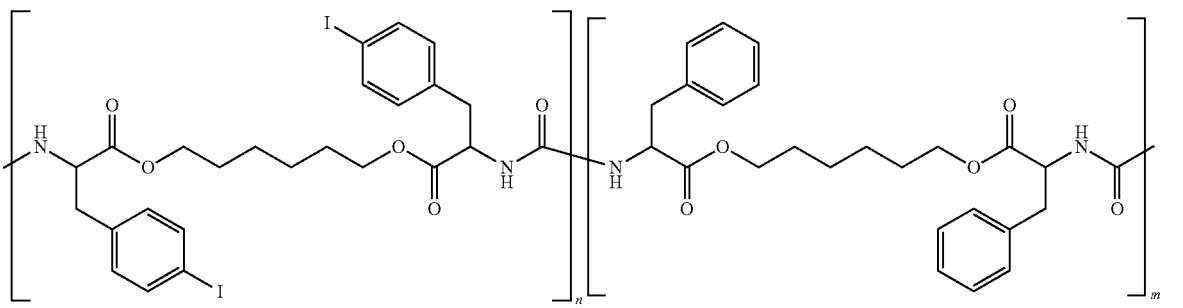

(III)

wherein n is a mole percentage of IPEU segments from about 1 to about 100; and m is a mole percentage of PEU segments from about 0 to about 99. In some of these embodiments, n is a mole percent of from about 1 to about 80. In some of these embodiments, n is a mole percent of from about 1 to about 60. In some of these embodiments, n is a mole percent of from about 1 to about 40. In some of these embodiments, n is a mole percent of from about 1 to about 20. In some of these embodiments, n is a mole percent of from about 20 to about 80. In some of these embodiments, m is a mole percent of from about 0 to about 99. In some of these embodiments, m is a mole percent of from about 0 to about 80. In some of these embodiments, m is a mole percent of from about 0 to about 60. In some of these embodiments, m is a mole percent of from about 0 to about 40. In some of these embodiments, m is a mole percent of from about 0 to about 20. In some of these embodiments, m is a mole percent of from about 20 to about 80.

In some embodiments, the PEUs of the present invention may be branched. In some of these embodiments, as will be discussed further below, the PEUs of the present invention may be formed by the homopolymerization of branched monomers having three or more amino acids, at least some of which are functionalized with a relatively large radiopaque atom such as iodine or boron. In some other of these embodiments, the PEUs of the present invention may be formed by the copolymerization of two or more different branched monomers having three or more amino acids, at least some of which are functionalized with a relatively large radiopaque atom such as iodine or boron. In some other of these embodiments, the PEUs of the present invention may be formed by the copolymerization of one or more branched monomers having three or more amino acids and one or more of the linear monomers described above, provided that at least some of these monomers are functionalized with a relatively large radiopaque atom such as iodine or boron.

In some embodiments, the PEUs of the present invention may have a weight average molecular weight ($M_w$) of from about 20 kDa to about 500 kDa. In some embodiments, the PEUs of the present invention may have a weight average molecular weight ($M_w$) of from about 20 kDa to about 250 kDa. In some embodiments, the PEUs of the present invention may have a weight average molecular weight ($M_w$) of from about 20 kDa to about 100 kDa. In some embodiments, the PEUs of the present invention may have a weight average molecular weight ($M_w$) of from about 20 kDa to about 50 kDa. In some embodiments, the PEUs of the present invention may have a weight average molecular weight ($M_w$) of from about 50 kDa to about 90 kDa.

In addition, it has been found that while the thermal properties of the PEUs according to embodiments of the present invention differ according to their specific composition of the PEUs, they are dependent upon the iodine content of the PEU. In general, it has been found that as iodine content increases, there is a corresponding increase in the thermal stability, as measured by the $T_g$ and TGA (5% weight loss temperature) of the polymer. (See Table, 2 below).

Similarly, it has been found that the mechanical properties of the PEUs according to embodiments of the present invention are also dependent upon the iodine (IPEU) content of the polymer. (See FIG. 1A-B) As set forth above, for example, it has been found that after a certain point which will depend upon the molecular weight of the polymer, among other things, an increase in the iodine content of the polymer results in a corresponding increase in the brittleness of the polymer.

It has been found that the higher the iodine (IPEU) content of the polymer, the higher the higher the radiopacity of the polymer. Radiopacity of the PEUs of embodiments of the present invention may be determined qualitatively from radioimages (See e.g. FIGS. 2, 3A-C, 4A-C, 5, 6, 7A-D, 8, 9A-D, 10A-D, and 11A-D; see also, Watts, D. C., and McCabe, J. F., "Aluminium radiopacity standards for dentistry: an international survey," Journal of Dentistry 27 (1999) 73-78, the disclosure of which is hereby incorporated by reference in its entirety) or it may be calculated using Lambert Beer law which states that:

$$I = I_0 \exp(-\mu^* t) \qquad (1)$$

where t is material thickness, $I_0$ is intensity of incident X-ray, I is intensity of transmittance X-ray, $\mu$ is attenuation coefficient, and t time. Thus, X-ray attenuation coefficient $\mu$ may be experimentally obtained. The mass attenuation coefficient may be defined as $$\mu_m = \mu/\rho \qquad (2)$$

where $\rho$ is density of material. It indicates the radiopacity of materials. $\mu_m$ of the element may be obtained from National Institute of Standards and Technology (NIST) data base.

X-ray attenuation when interacting with matter may be described in terms of photoelectric absorption and Compton scattering. Photoelectric absorption ($\mu_m$) can be described by the Bragg-Pierce law which sates that:

$$\mu_m = KZ^4\lambda^3 \qquad (3)$$

where K is a constant; Z is the atomic number of absorbing element; and $\lambda$ is the wavelength of absorbed X-rays. The probability of Compton scattering is directly proportional to electron density and the density of material. Thus empirical equation of X-ray attenuation when interacting with matter could be summarized as following:[4]

$$\mu_m = k\lambda^3 Z^4 + 0.2 \qquad (4)$$

where k is proportionality constant, which changes with atomic number and atomic shells; $\lambda$ is the wavelength of absorbed X-rays; and Z is the atomic number of absorbing element. So the ability of an element to attenuate X-rays is correlated with the atomic number of the element to the fourth power. Accordingly, the more large (relatively high atomic number) iodine or boron atoms in the polymer, the higher the calculated radiopacity will be.

In a second aspect, embodiments of the present invention are directed to methods of making the iodinated phenylalanine-based polymers described above. In general outline, the iodinated phenylalanine-based homopolymers or copolymers of the present invention are synthesized by a two-step step-growth polymerization process from one or more functionalized amino acids (including at least some iodine or boron functionalized phenylalanine molecules) and a linear or branched polyol, which are reacted to form an acid salt of a functionalized polyester compound having two or more amino acid end groups. These functionalized polyester monomers are then polymerized to form an iodinated phenylalanine-based poly(ester urea) polymer.

The reaction of the polyol with the amino acid to create an amino acid functionalized monomer can be achieved in any number of ways generally known to those of skill in the art. Generally, a condensation reaction at temperatures exceeding the boiling point of water involving a slight molar excess (~2.1 eq.) of the acid relative to the hydoxy groups is sufficient to enable the reaction to proceed. The presence of toluene sulphonic acid is necessary to protonate the amine on the amino acid and ensure that trans amidation reactions do not occur at higher conversions.

In some embodiments, the radiopaque phenylalanine-based copolymers described above may be synthesized as shown in Scheme 1.

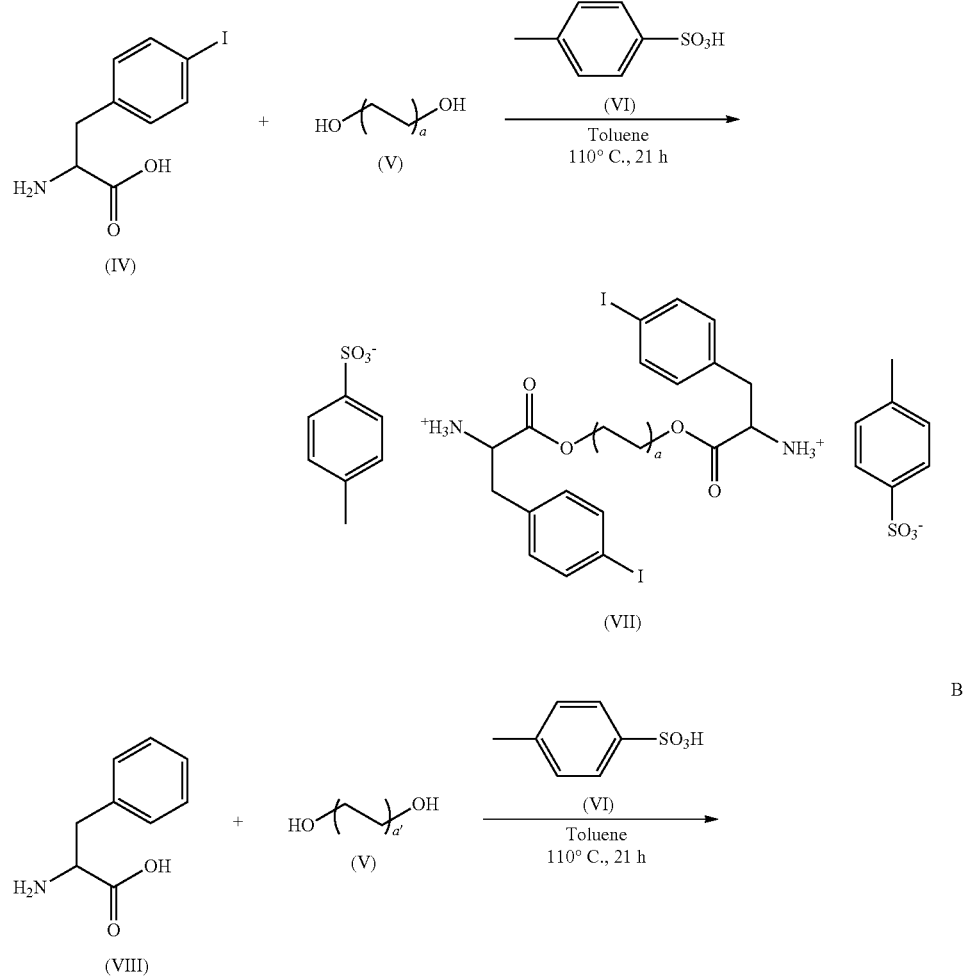

Scheme 1

-continued
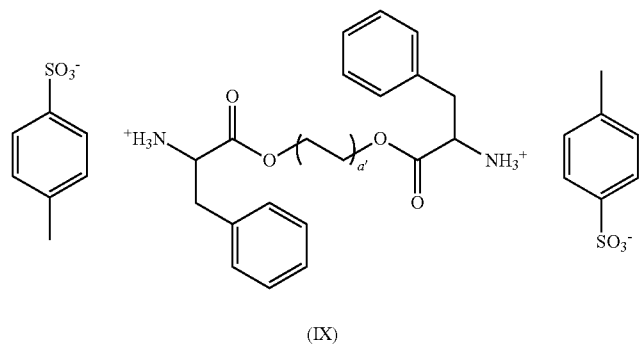
(IX)
Step 2
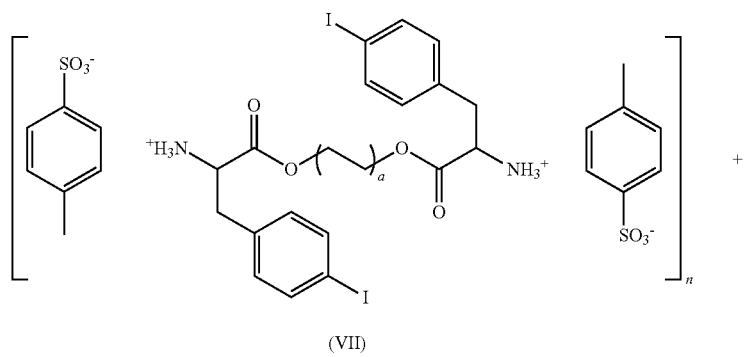
(VII)
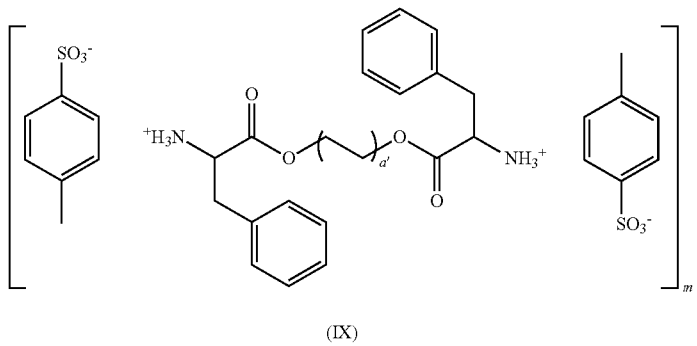
(IX)
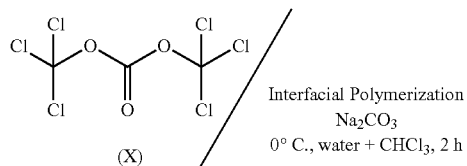
(X)
Interfacial Polymerization
Na₂CO₃
0° C., water + CHCl₃, 2 h -continued

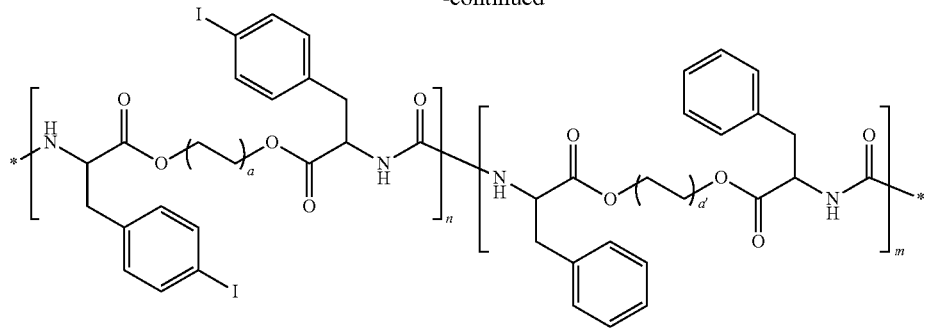

(II)

wherein a is an integer from about 2 to about 20, a' is an integer from about 2 to about 20, n is a mole percentage from about 1 to about 99, and m is a mole percentage from about 0 to about 99.

In these embodiments, the monomer that will form the IPEU segments and the monomer that will form the non-functionalized PEU segments of the PEUs of the present invention are prepared separately as shown in Step 1 of Scheme 1, above. Reactions A and B of Step 1 of Scheme 1 are substantially identical except for the first starting material, with Reaction A using an iodine functionalized L-phenylalanine molecule and Reaction B using a non-functionalized amino acid molecule. While Reaction A of Step 1 of Scheme 1 shows an iodine functionalized L-phenylalanine molecule, it should be understood that the present invention is not so limited and embodiments where the L-phenylalanine molecule of Reaction A is functionalized with a suitable radiopaque atom other than iodine are within the scope of the present invention. Suitable radiopaque atoms other than iodine may include, without limitation, boron. In some embodiments, the first starting material in Reaction A of Step 1 of Scheme 1 may be 4-iodo-L-phenylalanine and is commercially available from VWR International LLC (Radnor, Pa.).

The first starting material in Reaction B of Step 1 of Scheme 1 does not contain a radiopaque atom. While Reaction B of Step 1 of Scheme 1 shows L-phenylalanine as the first starting material, it should be understood that the first starting material may be any α-amino acid other than proline. In some embodiments, the first starting material may be alanine (ala-A); arginine (arg-R); asparagine (asn-N); aspartic acid (asp-D); cysteine (cys-C); glutamine (gln-Q); glutamic acid (glu-E); glycine (gly-G); histidine (his-H); isoleucine (ile-I); leucine (leu-L); lysine (lys-K); methionine (met-M); phenylalanine (phe-F); serine (ser-S); threonine (thr-T); tryptophan (trp-W); tyrosine (tyr-Y); valine (val-V) or combinations thereof. In some embodiments, the first starting material in Reaction B of Step 1 of Scheme 1 may be L-phenylalanine and is commercially available from Sigma Aldrich Company LLC (St. Louis, Mo.) or Alfa Aesar (Ward Hill, Mass.).

In both Reactions A and B of Step 1 of Scheme 1, the first starting material is reacted with a linear or branched polyol having from 2 to 60 carbon atoms. In some embodiments, the polyol has from 2 to 40 carbon atoms. In some embodiments, the polyol has from 2 to 20 carbon atoms. In some embodiments, the polyol has from 2 to 10 carbon atoms. In some embodiments, the polyol may be a diol, triol, or tetraol.

The polyol shown in both Reactions A and B of Step 1 of Scheme 1, is a diol having from 2 to 20 carbon atoms. In some embodiments, the polyol is a diol having from 2 to 17 carbon atoms. In some embodiments, the polyol is a diol having from 2 to 13 carbon atoms. In some embodiments, the polyol is a diol having from 2 to 10 carbon atoms. In some embodiments, the polyol is a diol having from 10 to 20 carbon atoms. In some embodiments, the polyol is a diol having 3 carbon atoms. Suitable polyols may include, without limitation, 1,6-hexanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, 2-butene-1,4-diol, 3,4-dihydroxy-1-butene, 7-octene-1,2-diol, 3-hexene-1,6-diol, 1,4-butynediol, trimethylolpropane allyl ether, 3-allyloxy-1,2-propanediol, 2,4-hexadiyne-1,6-diol, 2-hydroxymethyl-1,3-propanediol, 1,1,1-Tris (hydroxymethyl) propane, 1,1,1-tris(hydroxymethyl)ethane, pentaerythritol, di(trimethylolpropane) dipentaerythritol and combinations thereof. In the embodiments, the polyol may be 1,6-hexanediol and is commercially available from Sigma Aldrich Company LLC (St. Louis, Mo.) or Alfa Aesar (Ward Hill, Mass.).

In both Reactions A and B the first starting material and the polyol are dissolved in a suitable solvent with a suitable acid and heated to a temperature of from 110° C. to about 114° C. and refluxed for from about 20 hours to about 48 hours to form the salt of a monomer having two or more amino acid residues separated by from about 2 to about 60 carbon atoms, depending upon the polyol used. (See Scheme 1, above). One of ordinary skill in the art will be able to select a suitable acid without undue experimentation. In some embodiments, the acid used may be p-toluene sulfonic acid monohydrate. One of ordinary skill in the art will also be able to select a suitable solvent without undue experimentation. Suitable solvents include without limitation, toluene, dichloromethane, chloroform, dimethylformamide (DMF) or combinations thereof.

In some embodiments, the solvent used may be toluene. As will be apparent to those of skill in the art, steps should be taken to protect the amine groups on the monomer intermediates to prevent transamidation. One of ordinary skill in the art will be able to select a suitable counter-ion without undue experimentation. Materials capable of producing suitable protecting counter-ions may include without limitation, p-toluene sulfonic acid monohydrate, chlorides, bromides, acetates. trifloroacetate, or combinations thereof. In some embodiments, the monomer intermediate formed in Reaction A of Step 1 of Scheme 1 may be the di-p-toluene sulfonic acid salt of bis-4-I-L-phenylalanine-1,6-hexanediol-diester (1-IPHE-6 monomer). In some embodiments, the monomer intermediate for Reaction B of Step 1 of Scheme 1 may be the di-p-toluene sulfonic acid salt of bis-L-phenylalanine-1,6-hexanediol-diester (1-PHE-6 monomer).

The crude product of Reactions A and B may be purified using any means known in the art for that purpose. In some embodiments, the crude product of Reactions A of Step 1 of Scheme 1 may be purified by first vacuum filtering the crude product to remove the residual solvent and decolorizing it in activated carbon to remove any residual salts or unreacted monomers. The crude product of Reaction A may then be recrystallized from boiling water from 1 to 10 times to produce a purified product. In some embodiments, the crude product of Reaction A may be recrystallized from boiling water from 1 to 10 times to produce a purified product. In some embodiments, the crude product of Reactions B of Step 1 of Scheme 1 may be purified by first vacuum filtering the crude product to remove the residual solvent and decolorizing it in activated carbon to remove any residual salts or unreacted monomers. The crude product of Reaction B may then be recrystallized from a 1:1 mixture of water and alcohol to produce a purified product. In some embodiments, the crude product of Reaction B may then be recrystallized from a 1:1 mixture of water and alcohol from 1 to 10 times to produce a purified product.

In Step 2 of Scheme 1, the monomers of Step 1 are polymerized using an interfacial polymerization method to form radiopaque phenylalanine-based copolymers according to one or more embodiments of the present invention. As used herein interfacial polymerization refers to polymerization that takes place at or near the interfacial boundary of two immiscible fluids. In these embodiments, the protected monomer intermediates of Steps 1A and B are combined in a desired molar ratio with a first fraction of a suitable organic water soluble base such as sodium carbonate, potassium carbonate, sodium bicarbonate, or potassium bicarbonate and dissolved in water using mechanical stirring and a warm water bath (approximately 35° C.).

To introduce the urea bond to the resultant amino acid functionalized monomer, phosgene, diphosgene or triphosgene is employed. Diphosgene (a liquid) and triphosgene (a solid crystal) may be found more suitable than phosgene because they are generally appreciated as safer substitutes to phosgene, which is a toxic gas. The reaction of an amino acid functionalized monomer with triphosgene, diphosgene or phosgene to create an amino acid-based PEU can also be achieved in any number of ways generally known to those of skill in the art.

In some of these embodiments, the counter-ion protected monomer intermediates of Steps 1A and 1B are combined in a molar ratio of from about 1:99 to about (99:1) counter-ion protected monomer intermediate of Steps 1A to counter-ion protected monomer intermediates of Steps 1B. In some of these embodiments, molar ratio of the counter-ion protected monomer intermediates of Step 1A to those of Step 1B is from about 1:4 to about 4:1. In some of these embodiments, molar ratio of the counter-ion protected monomer intermediates of Step 1A to those of Step 1B is from about 1:3 to about 3:1. In some of these embodiments, molar ratio of the counter-ion protected monomer intermediates of Step 1A to those of Step 1B is from about 1:2 to about 2:1. In some of these embodiments, the molar ratio of the counter-ion protected monomer intermediate of Step 1A to that of Step 1B is about 1:1. In some of these embodiments, the molar ratio of the counter-ion protected monomer intermediate of Step 1A to that of Step 1B is about 1:4. In some of these embodiments, the molar ratio of the counter-ion protected monomer intermediate of Step 1A to that of Step 1B is about 3:4.

In some embodiments, the PEUs of the present invention may comprise from about 1 mole percent to about 100 mole percent I-PEU segments. In some embodiments, the PEUs of the present invention may comprise from about 1 mole percent to about 75 mole percent I-PEU segments. In some embodiments, the PEUs of the present invention may comprise from about 1 mole percent to about 50 mole percent I-PEU segments. In some embodiments, the PEUs of the present invention may comprise from about 1 mole percent to about 25 mole percent I-PEU segments. In some embodiments, the PEUs of the present invention may comprise from about 25 mole percent to about 75 mole percent I-PEU segments.

In some embodiments, the PEUs of the present invention may comprise from about 0 mole percent to about 99 mole percent non-functionalized PEU segments. In some embodiments, the PEUs of the present invention may comprise from about 25 mole percent to about 99 mole percent non-functionalized PEU segments. In some embodiments, the PEUs of the present invention may comprise from about 50 mole percent to about 99 mole percent non-functionalized PEU segments. In some embodiments, the PEUs of the present invention may comprise from about 75 mole percent to about 99 mole percent non-functionalized PEU segments. In some embodiments, the PEUs of the present invention may comprise from about 25 mole percent to about 75 mole percent non-functionalized PEU segments.

In one or more embodiments, the reaction is then cooled to a temperature of from about −10° C. to about 2° C. and an additional fraction of an organic water soluble base such as sodium carbonate, potasium carbonate, sodium bicarbonate, or potassium bicarbonate is dissolved in water and then added to the reaction mixture. The reaction may be cooled by any means known in the art for that purpose, including, without limitation, ice baths, water baths, or recirculating coolers. A first fraction of a PEU forming compound such as triphosgene or phosgene is dissolved in a suitable solvent, such as distilled chloroform or dichloromethane, and is then added to the reaction mixture. After a period of from about 2 to about 60 minutes, a second fraction of the PEU forming compound (such as triphosgene or phosgene) is dissolved in a suitable solvent, such as distilled chloroform or dichloromethane, and added dropwise to the reaction mixture over a period of from about 0.5 to about 6 hours to produce a crude copolymer containing IPEU segments and non-functionalized PEU segments.

The crude product of Step 2 of Scheme 1 may be purified using any means known in the art for that purpose. In some embodiments, the crude product of Step 2 of Scheme 1 may be purified by transferring it into a separatory funnel and precipitating it into boiling water.

In some embodiments, radiopaque PEU polymers according to the present invention may be synthesized by homopolymerization as shown in Scheme 2 below:

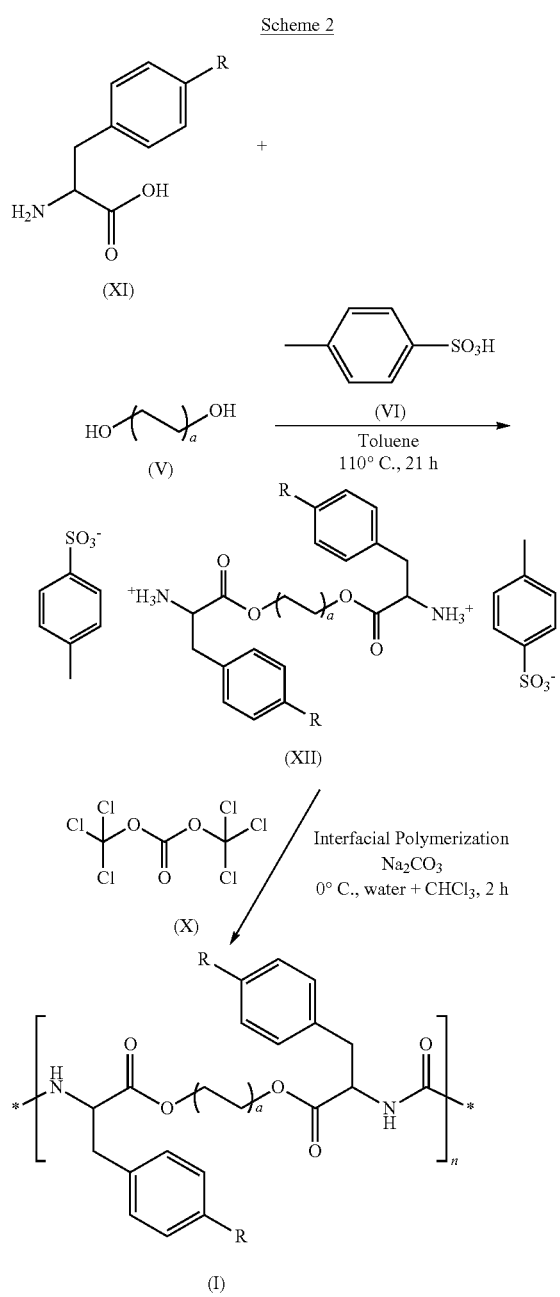

Scheme 2 wherein R is H and/or a large radiopaque atom such as iodine, boron or combinations thereof, a is an integer from about 1 to about 10, and n is an integer from about 10 to about 1000. The amino acid starting material (XI) shown in Scheme 2 is a functionalized or non-functionalized L-phenylalanine, but is should be appreciated that the present invention is not to be so limited. In various embodiments of the present invention, the amino acid starting material (XI) may be any amino acid or combination of amino acids other than proline, provided at least some of the amino acids used are functionalized with a large radiopaque atom, such as iodine or boron. In these embodiments, the iodine content of the homopolymer may be regulated by controlling the ratio of iodine functionalized amino acids used to form the monomer salt. In some of these embodiments, the amino acid starting material (XI) may comprise L-phenylalanine, which is commercially available from Sigma Aldrich Company LLC (St. Louis, Mo.) or Alfa Aesar (Ward Hill, Mass.) and 4-iodo-L-phenylalanine, which is commercially available from VWR International LLC (Radnor, Pa.).

In these embodiments, the amino acid starting material (XI) is then reacted with a linear or branched polyol (V) to for an acid salt of the monomer used to form the PEU (XII), as shown in Schemes 1 and 2, and discussed in detail above. Any of the linear or branched polyols discussed above may be used to form the acid salt of the monomer used to form the PEU.

In these embodiments, the PEU is formed largely as set forth above except that only one monomer salt is used. The monomer salt is combined with a first fraction of a suitable base such as sodium carbonate, potassium carbonate, sodium bicarbonate, or potassium bicarbonate, and dissolved in water using mechanical stirring and a warm water bath (approximately 35° C.). The reaction is then cooled to a temperature of from about −10° C. to about 2° C. and an additional fraction of base is dissolved in water and added to the reaction mixture. Next, a first fraction of a PEU forming compound is dissolved in a suitable solvent and added to the reaction mixture. As used herein, the term "PEU forming compound" refers to a compound capable of placing a carboxyl group between two amine groups, thereby forming a urea bond and includes, without limitation, triphosgene, diphosgene, or phosgene. As set forth above, diphosgene (a liquid) and triphosgene (a solid crystal) are understood to be more suitable than phosgene because they are generally appreciated as safer substitutes to phosgene, which is a toxic gas. One of ordinary skill will be able to select a suitable solvent for the PEU forming compound without undue experimentation. Selection of a suitable solvent for the PEU forming compound will, of course, depend upon the particular compound chosen, but may include, without limitation, distilled chloroform dichloromethane, or dioxane. After a period of from about 2 to about 60 minutes, a second fraction of the (such as triphosgene or phosgene) is dissolved in a suitable solvent, such as distilled chloroform or dichloromethane, and added dropwise to the reaction mixture over a period of from about 0.5 to about 12 hours to produce a crude homopolymer containing both iodine functionalized and non-iodine functionalized amino acid residues. The crude product may be purified using any means known in the art for that purpose. In some embodiments, the crude homopolymer product may be purified by transferring it into a separatory funnel and precipitating it into boiling water.

In some other embodiments, the radiopaque PEU polymers according to the present invention may be synthesized by copolymerizing two or more batches of monomer salts, made as set forth above with respect to the homopolymer, with each batch of monomer salts having a different and distinct combination of amino acid residues. Once prepared, these monomer salts may be copolymerized as set forth above. Again, in order for the PEU formed from these monomer salts to be radiopaque, at least some of the amino acid residues in monomer salts forming the copolymer must be functionalized with a radiopaque atom, such as iodine or boron.

The radiopaque PEUs of various embodiments of the present invention can be used to make or add opacity to a wide variety of degradable objects implanted in a body or other place where its presence and/or location may be determined by X-ray. In some embodiments, radiopaque PEUs according to various embodiments of the present invention may be used to form, without limitation, tissue scaffolds, a 3D printed material, drug eluting scaffold, thin film or coating. Any suitable method known in the art for implantable objects using the PEU polymers may be used including, without limitation, extrusion based 3-dimensional (3D) printing, extrusion, injection molding, or melt spinning. In some embodiments, the radiopaque PEUs according to various embodiments of the present invention may be used as an additive to add radiopaque properties to other materials.

Experimental

In order to evaluate the of amino acid-based poly(ester urea)s (PEUs) of embodiments of the present invention, homopolymers of the 1-IPHE-6 monomer and 1-PHE-6 monomers (poly(1-IPHE-6) and poly(1-PHE-6), respectively) were prepared and compared to copolymers of these monomers (poly(1-IPHE-6)-co-poly(1-PHE-6)s) with varied iodine content (poly(1-IPHE-6)$_{0.44}$-co-poly(1-PHE-6)$_{0.55}$ and poly(1-IPHE-6)$_{0.24}$-co-poly(1-PHE-6)$_{0.76}$). The resulting polymers were characterized using a number of chemical, thermal and mechanical methods. Micro-computed tomography (μ-CT) 2D projections of polymers with varied iodine content were compared to established aluminum contrast standards. Porous 3D scaffolds were made with varied iodine content, and were characterized for radiopacity and compression modulus. Cell viability and spreading tests were carried out to look for potential cytotoxicity and indications of atypical phenotype.

Figure 12:
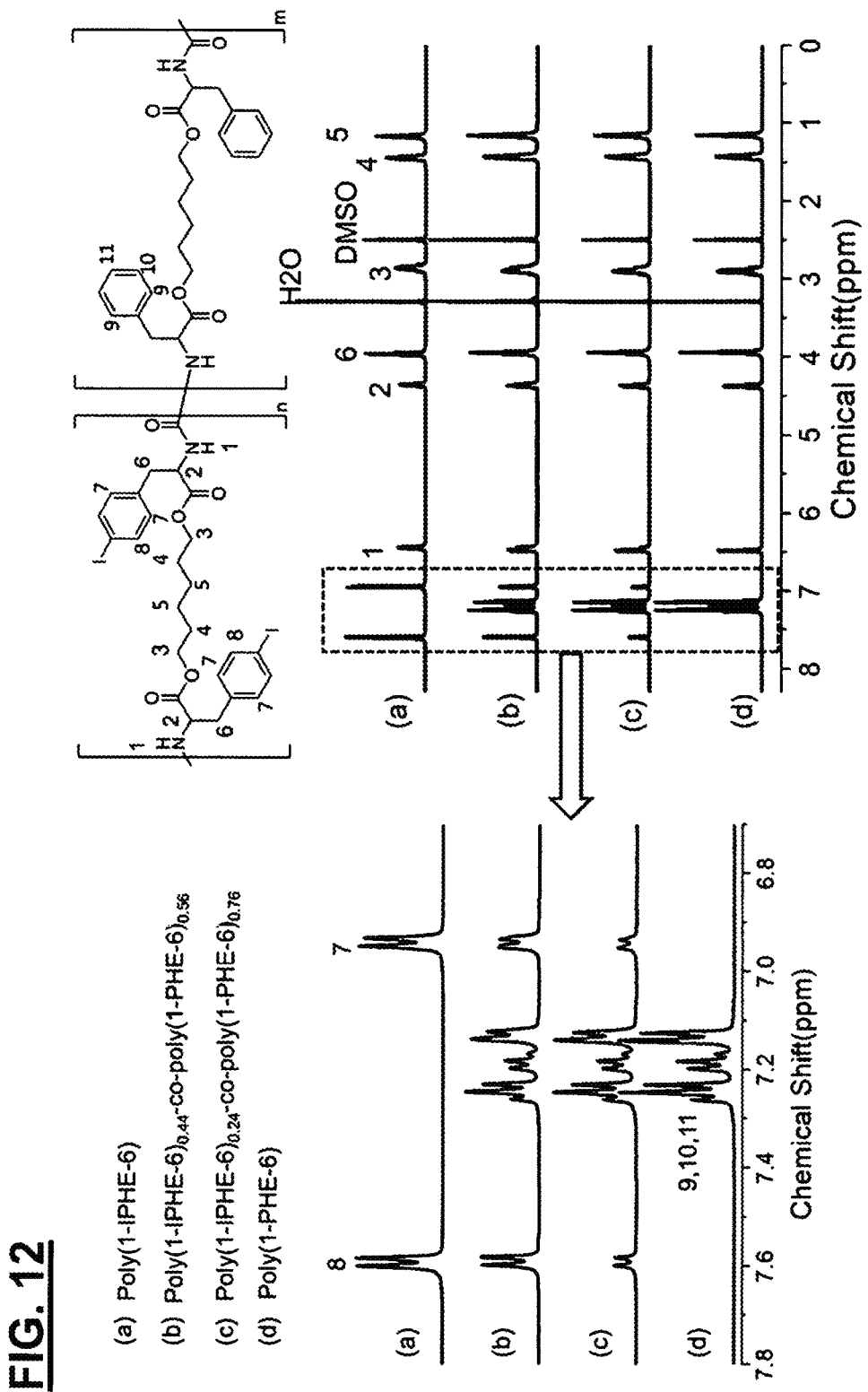
FIG. 12 is a comparison of the $^1$H-NMR (DMSO-$d_6$) spectra of PEUs according to one or more embodiments of the present invention, wherein: spectra (a) is of a homopolymer of the 1-IPHE-6 monomer (poly(1-IPHE-6), which has ring signals at 6.95 and 7.6 ppm, characteristic of a para-substituted aromatic ring; spectra (b) is of a copolymer of the 1-IPHE-6 monomer and 1-PHE-6 monomer at a 3:4 molar ratio (44% poly(1-IPHE-6) and 56% poly(1-PHE-6) (poly(1-IPHE-6)$_{0.44}$-co-poly(1-PHE-$_6$)$_{0.56}$); (c) is of a copolymer of the 1-IPHE-6 monomer and 1-PHE-6 monomer at a 1:4 molar ratio (24% poly(1-IPHE-6) and 76% poly(1-

Chemical structure and polymer composition for these PEUs were determined using NMR and FT-IR spectroscopy. In FIG. 12, the urea peak at 6.5 ppm shows the successful synthesis of the four different PEU polymers. For poly(1-PHE-6), the aromatic hydrogen peaks appear around 7.1 to 7.3 ppm. However, substitution of one hydrogen atom with an iodine atom shifts the other aromatic protons to 6.95 ppm and 7.6 ppm. For copolymers, the aromatic protons have characteristic poly(1-PHE-6) and poly(1-IPHE-6) resonances. With the increase of iodine content, the poly(1-IPHE-6) characteristic peak intensity increases and the poly(1-PHE-6) characteristic peak intensity decreases. The copolymer composition can therefore be calculated by integration of these peaks from $^1$H-NMR results. By using the hydrogen attached to tertiary carbons at 4.35-4.39 ppm as the reference peak, the integration of the aromatic rings should change with different iodine content. For example, for poly(1-PHE-6) there are 10 hydrogen atoms located on the aromatic ring and 2 are attached to the tertiary carbon for every repeat unit with a ratio of 5. For poly(1-IPHE-6), the ratio is 4.

For copolymers, the ratio should be between 4 and 5, and indicates the extent of iodination imparted to the polymer. As listed in the first three columns of Table 1, the NMR normalized integration ratio of poly(1-PHE-6), poly(1-IPHE-6) and the two copolymers are 4.99, 3.98, 4.76 and 4.56, respectively. The corresponding poly(1-IPHE-6) content in the polymers are therefore calculated to be 0%, 100%, 24% and 44%. This result was consistent with the feed ratio. $^{13}$C-NMR (See, FIG. 13) supports these results. The copolymer composition could also have been obtained from FT-IR (See, FIG. 14).

For FT-IR, baseline deduction and normalization of the urea group peak absorbance at 3398 cm$^{-1}$ were carried out for all absorbance spectra. The C-I absorbance peak intensity at 1007 cm$^{-1}$ increases with increasing iodine content, which is set as the analytical peak. For poly(1-PHE-6) and poly(1-IPHE-6), the peak intensity at 1007 cm$^{-1}$ is 0 and 0.29, respectively. Thus, it appears that the copolymer intensity at 1007 cm$^{-1}$ was entirely contributed by the iodinated part. As such, the ratio of the C-I peak intensity of the copolymers to that of poly(1-IPHE-6) (0.29) shows the iodinated composition in the copolymer to be 24% and 41%, respectively, which again confirms the NMR result (See Table 1, below). Both NMR and FT-IR spectroscopy demonstrate the successful synthesis of iodine-functionalized PEUs. It should be appreciated that the content of iodine can be easily adjusted via simply changing the feed ratio of the different monomers.

TABLE 1

PEUs composition from $^1$H-NMR and FT-IR

| 1-IPHE-6 monomer feed ratio | NMR normalized integration ratio* | Poly(1-IPHE-6) content in polymer from NMR*† | FT-IR normalized peak height# | Poly(1-IPHE-6) content in polymer from FT-IR#‡ |
|---|---|---|---|---|
| 100% | 3.98 | 100% | 0.29 | 100% |
| 43% | 4.56 | 44% | 0.12 | 41% |
| 20% | 4.76 | 24% | 0.07 | 24% |
| 0 | 4.99 | 0 | 0 | 0 |

*NMR normalized integration ratio = integration of analytical peak/integration of reference peak Reference peak: hydrogen attached to tertiary carbon (Chemical shift: 4.35-4.39 ppm). Analytical peak: hydrogen in aromatic ring (Chemical shift: 6.93-7.60 ppm)
†Poly(1-IPHE-6) content in copolymer from NMR = (5 − NMR normalized integration ratio) × 100%.
Reference peak: urea group peak absorbance at 3398 cm$^{-1}$. Analytical peak: C-I absorbance at 1007 cm$^{-1}$.
‡Poly(1-IPHE-6) content in copolymer = (FT-IR normalized peak height/0.29) × 100

As set forth above, in some embodiments, the radiopaque PEUs of the present invention are expected to be used as parts of implantable medical devices, which generally are fabricated using melt processing. A high degradation temperature is therefore preferred for the manufacture of these implantable devices. The thermal stability of these PEUs was characterized using TGA (See, Table 2). The TGA results show that the 5% weight loss temperatures for poly(1-PHE-6), poly(1-IPHE-6)$_{0.24}$-co-poly(1-PHE-6)$_{0.76}$, poly(1-IPHE-6)$_{0.44}$-co-poly(1-PHE-6)$_{0.56}$ and poly(1-IPHE-6) are 277, 287, 297 and 303° C., respectively. This suggests that iodine incorporation increases the thermal stability of PEUs. The glass transition temperatures were obtained by DSC (See, FIG. 15 and Table 2). The glass transition temperatures of poly(1-PHE-6), poly(1-IPHE-6)$_{0.24}$-co-poly(1-PHE-6)$_{0.76}$, poly(1-IPHE-6)$_{0.44}$-co-poly(1-PHE-6)$_{0.56}$ and poly(1-IPHE-6) are 59, 65, 71 and 88° C., respectively. All four materials have glass transition temperatures far above physiological temperature, which is near 37° C. It believed that the radiopaque PEUs of embodiments of the present invention are suitable for implantable device manufacturing. The DSC results show that incorporation of iodine in poly(1-PHE-6) can increase the glass transition temperature, which is consistent with previously published results. It is believed that this observation may be attributed to two issues. First, iodine is polarizable, which increases both the inter- and intra-chain interaction and hence, reduces the segmental mobility of polymer chains. Second, iodine is bulky, which hinders the mobility of polymer chains. Both of these properties become enhanced with increasing iodine content, causing a resultant increase in the glass transition temperature of PEUs with increasing iodine content.

TABLE 2

Characterization summary of PEUs

| Sample | $M_n$ | $M_w$ | $Đ_M$ | $T_d/°C$ (TGA) | $T_g/°C$ (DSC) |
|---|---|---|---|---|---|
| Poly(1-PHE-6) | 87k | 148k | 1.7 | 277 | 59 |
| Poly(1-IPHE-6)$_{0.24}$-co-poly(1-PHE-6)$_{0.76}$ | 181k | 307k | 1.7 | 287 | 65 |
| Poly(1-IPHE-6)$_{0.44}$-co-poly(1-PHE-6)$_{0.56}$ | 117k | 238k | 2.0 | 297 | 71 |
| Poly(1-IPHE-6) | 88k | 147k | 1.7 | 303 | 88 |

Figure 1A:
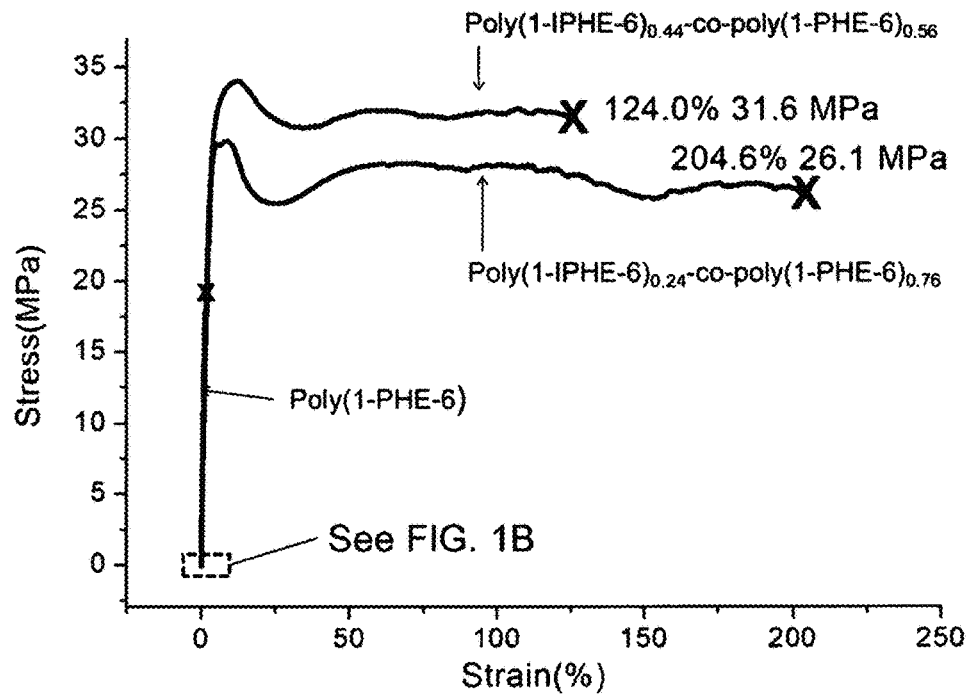
FIG. 1A is a graph showing the stress-strain curves of poly(1-PHE-6), poly(1-IPHE-6)$_{0.24}$-co-poly(1-PHE-6)$_{0.76}$ and poly(1-IPHE-6)$_{0.44}$-co-poly(1-PHE-6)$_{0.56}$ measured by dynamic mechanical analysis with a strain rate of 2.5%/min at room temperature. Three samples were tested for each polymer film. The elastic moduli were obtained in the linear region of the stress-strain curve and the average value of three samples was calculated. Incorporation of iodine in poly(1-PHE-6) makes the normally brittle PEU more ductile. However, with increasing iodine content, the PEUs again becomes brittle. Poly(1-IPHE-6) homopolymer for example was too brittle to be measured by Dynamic Mechanical Analysis (DMA). The elastic moduli of PEUs decreased following iodine modification.
Figure 1B:
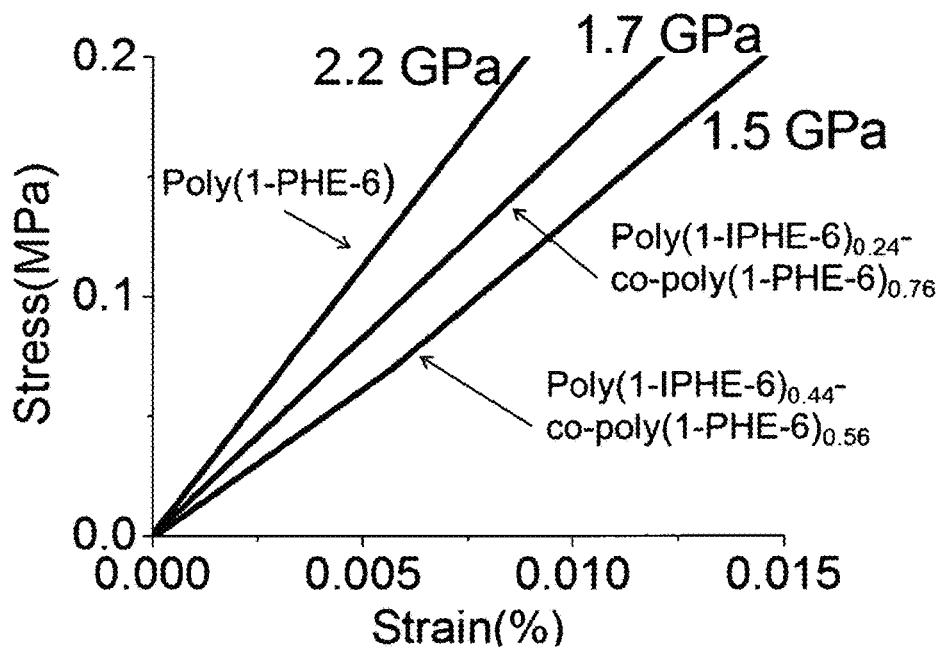
FIG. 1B is an enlargement of a section of the graph of FIG. 1A, showing the stress-strain curves of poly(1-PHE-6), poly(1-IPHE-6)$_{0.24}$-poly(1-PHE-6)$_{0.76}$ and poly(1-IPHE-6)$_{0.44}$-co-poly(1-PHE-6)$_{0.56}$ measured by dynamic mechanical analysis with a strain rate of 2.5%/min at room temperature. The elastic moduli of PEUs decreased following iodine modification.

The mechanical properties of bulk films made with these PEUs were also evaluated. FIG. 1A-B show the stress-strain curves of poly(1-PHE-6), poly(1-IPHE-6)$_{0.24}$-co-poly(1-PHE-6)$_{0.76}$ and poly(1-IPHE-6)$_{0.44}$-co-poly(1-PHE-6)$_{0.56}$ as obtained by DMA. The poly(1-PHE-6) film was brittle with no observable yield point, while both poly(1-IPHE-6)$_{0.24}$-co-poly(1-PHE-6)$_{0.76}$ and poly(1-IPHE-6)$_{0.44}$-co-poly(1-PHE-6)$_{0.56}$ were ductile with a tensile elongation at break of 205% and 124%, respectively. (See FIG. 1A) Elastic moduli were calculated in the low strain region for all three polymers. As shown in FIG. 1B, elastic moduli for poly(1-PHE-6), poly(1-IPHE-6)$_{0.24}$-co-poly(1-PHE-6)$_{0.76}$ and poly(1-IPHE-6)$_{0.44}$-co-poly(1-PHE-6)$_{0.56}$ are (2.2±0.1) GPa, (1.7±0.2) GPa, and (1.5±0.1) GPa, respectively. It was found that the incorporation of iodine decreased the moduli of poly(1-PHE-6). While not wishing to be bound by theory, it is believed that one possible reason for this is that bulky iodine atoms interrupt the regular packing of polymer chains and, as a result, the hydrogen-bonding networks of poly(1-PHE-6) are partially broken down. Less hydrogen bonding interaction leads to smaller elastic moduli for iodinated poly(1-PHE-6). It is believed that modification of poly(1-PHE-6) with iodine decreases the elastic modulus and also toughens poly(1-PHE-6). It has been found that the elongation at break shows a maximum at 205% for poly(1-IPHE-6)$_{0.24}$-co-poly(1-PHE-6)$_{0.76}$. This is possibly due to the competition of two major factors that determine the elongation at break of materials. As set forth above, the incorporation of a small amount of iodine atom may decrease hydrogen bonding interactions. The interaction between polymer chains is thereby reduced, which results in a higher elongation at break for poly(1-IPHE-6)$_{0.24}$-co-poly(1-PHE-6)$_{0.76}$ compared with poly(1-PHE-6). In addition, as set forth above, iodine atoms are polarizable, and have strong interactions with each other, which may hinder the sliding of polymer chains past one another. Accordingly, it has been found that with an increase of iodine content in the polymers, for example poly(1-IPHE-6)$_{0.44}$-co-poly(1-PHE-6)$_{0.56}$, the elongation at break decreases compared with poly(1-IPHE-6)$_{0.24}$-co-poly(1-PHE-6)$_{0.76}$. For poly(1-IPHE-6). The brittleness property is presumed to be attributed in part to the strong interactions between polarized iodine atoms.

The radiopathy of these PEUs were also evaluated. μ-CT testing shows that incorporation of iodine enhances the radiopacity of poly(1-PHE-6). FIG. 2 is a comparison of μ-CT projection images of PEUs according to embodiments of the present invention (left column) with reference aluminum stages with thicknesses of 0.5 mm, 1 mm, 1.5 mm, 2 mm and 2.5 mm, respectively (right column). Since aluminum atoms hinder X-ray transmission, the radiopacity of reference aluminum stages increases with larger thickness. By comparing the reference aluminum stages with PEU films with different iodine content, it is possible to assess the approximate radiopacity of iodinated PEUs.

FIG. 2 (left column) shows μ-CT images of poly(1-PHE-6), poly(1-IPHE-6)$_{0.24}$-co-poly(1-PHE-6)$_{0.76}$, poly(1-IPHE-6)$_{0.44}$-co-poly(1-PHE-6)$_{0.56}$ and poly(1-IPHE-6), respectively. The thickness of all films is 0.5 mm. It is clear from FIG. 2 that the radiopacity of iodinated PEUs increases with increasing iodine content, as is expected. By comparing the μ-CT results of poly(1-IPHE-6) with the reference, it is obvious that poly(1-IPHE-6) film has similar radiopacity to that of the aluminum reference with a thickness of 1 mm, poly(1-IPHE-6)$_{0.4}$-co-poly(1-PHE-6)$_{0.56}$ film has similar radiopacity to that of the aluminum reference with a thickness of 0.5 mm, and the radiopacity of poly(1-IPHE-6)$_{0.24}$-co-poly(1-PHE-6)$_{0.76}$ film is lower than the 0.5 mm thickness aluminum reference. Regardless of iodine content, the radiopacity is still much higher than that of the poly(1-PHE-6) film. The contrast of poly(1-PHE-6) is very weak since there is no heavy atom in the material. Hence it has been found that the radiopacity of polymers can be adjusted by controlling the content of iodine in the copolymer. Almost any implantable polymeric device needs radio contrast to distinguish it from neighboring tissues and to locate its position within the body. Since different tissues may have different radiopacity, it is believed that the radiopacity of polymeric implantable devices should change depending on their implantation location. As set forth above, the methods of the present invention provide a simple mechanism for regulating the iodine content, and therefore the opacity, of the PEUs, permitting them to be used for many different applications throughout the body.

Figure 3A:
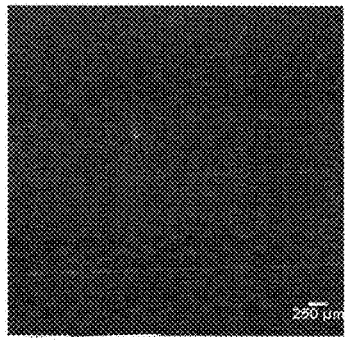
FIGS. 3A-C are images of reconstruction slices of Micro-CT 3D scanning of porous scaffolds made with PEUs according to embodiments of the present invention having different iodine contents, taken under the same scanning conditions.
Figure 3B:
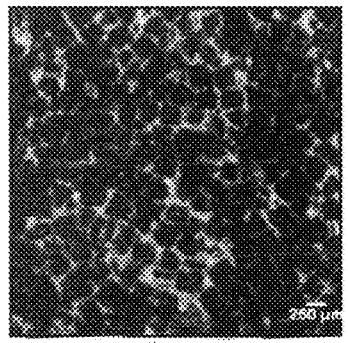
Figure 3C:
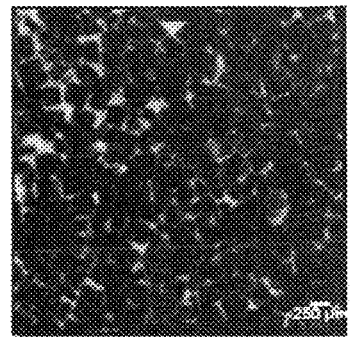
Figure 4A:
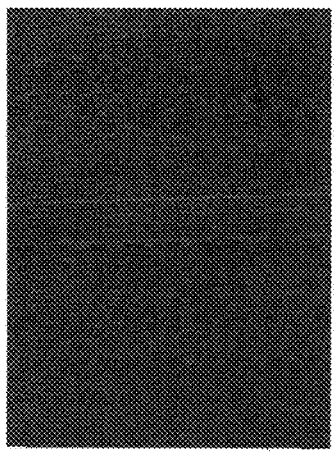
FIGS. 4A-C are images of reconstruction slices of Micro-CT 3D scanning of porous scaffolds made with PEUs according to embodiments of the present invention having different iodine contents, taken under the same scanning conditions.
Figure 4B:
Figure 4C:
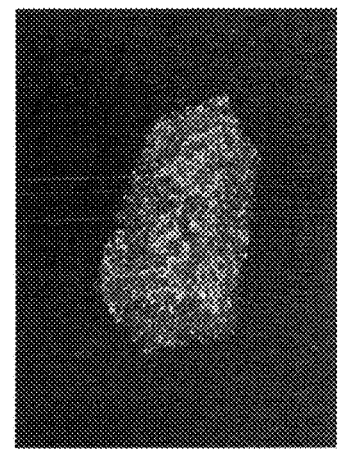
Figure 5:
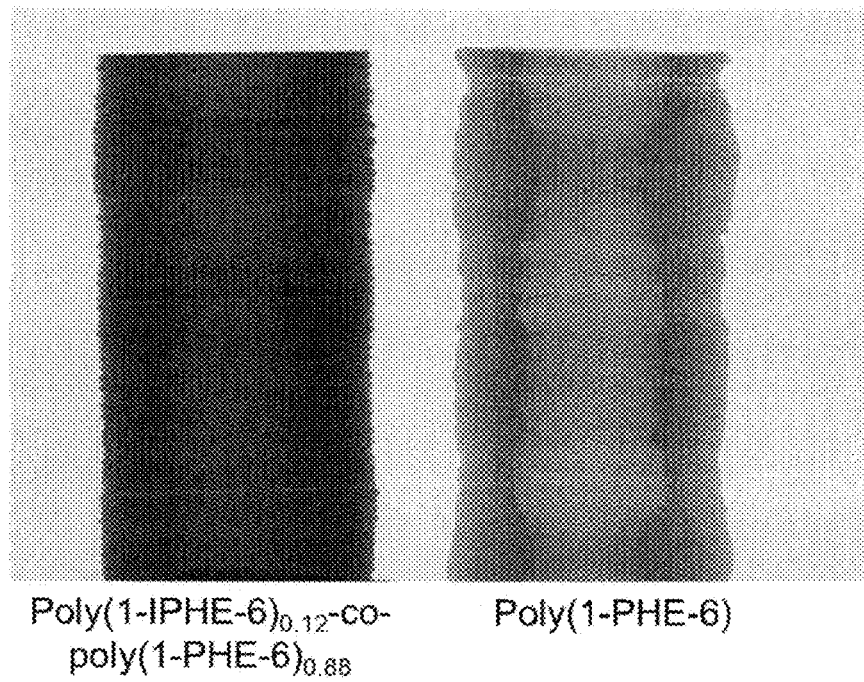
FIG. 5 is a μ-CT shadow projection of poly(1-IPHE-6)$_{0.12}$-co-poly(1-PHE-6)$_{0.88}$ (left) and poly(1-PHE-6) (right) tubular scaffolds. This images shows the radio contrast between conventional PEU and iodine functionalized PEU.
Figure 6:
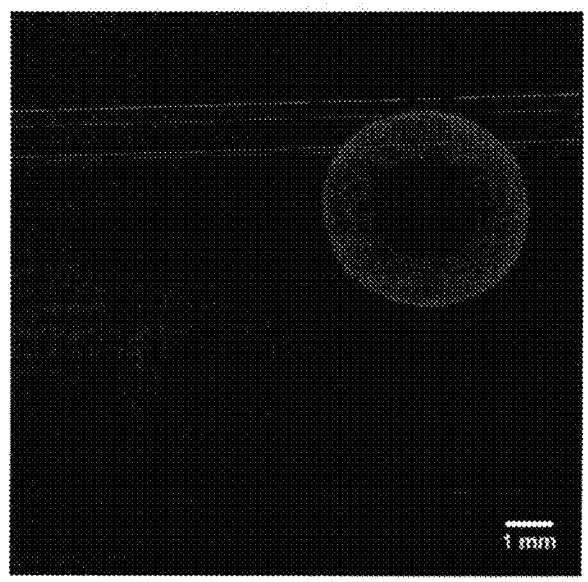
FIG. 6 is an image showing a reconstruction slice of poly(1-IPHE-6)$_{0.12}$-co-poly(1-PHE-6)$_{0.88}$ tubular scaffold (Right) and a reconstruction slice of poly(1-PHE-6) scaffold (Left), which is present but not visible.
Figure 9A:
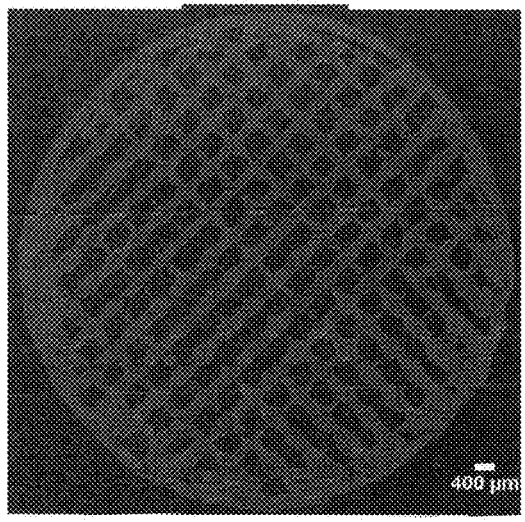
FIGS. 9A-B are reconstruction slices of poly(1-PHE-6) orthogonally knitted porous scaffolds.
Figure 9B:
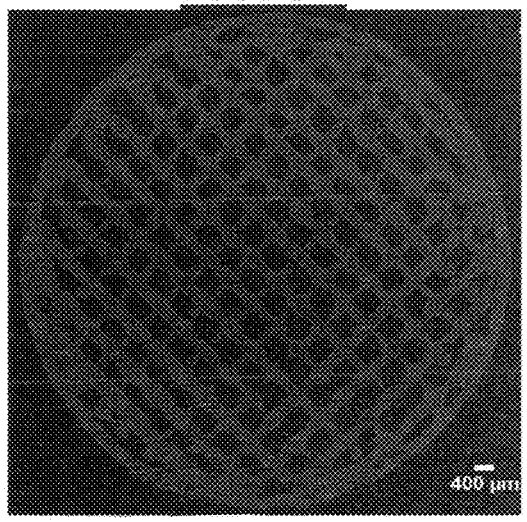
Figure 9C:
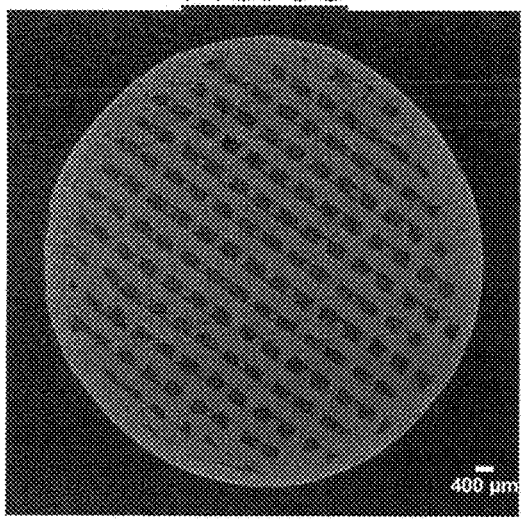
FIGS. 9C-D are reconstruction slices of a poly(1-IPHE-6)$_{0.12}$-co-poly(1-PHE-6)$_{0.88}$ orthogonally knitted porous scaffold.
Figure 9D:
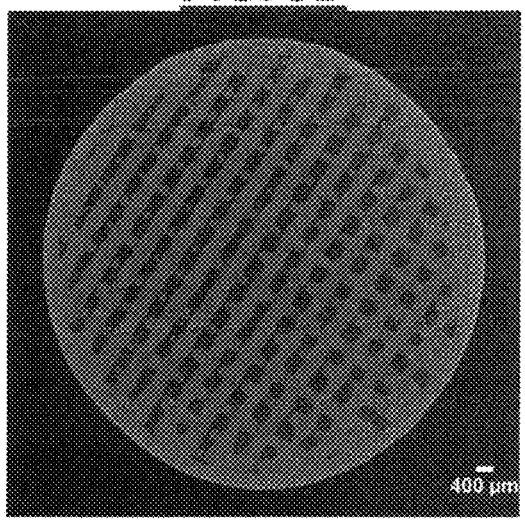
Figure 10A:
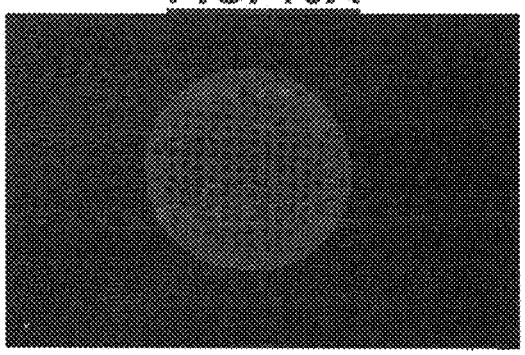
FIG. 10A-D are 3D reconstruction images showing a top view (FIG. 10A), elevated view (FIG. 10B), half sectional view (FIG. 10C), and quarter sectional view (FIG. 10D) of a of poly(1-PHE-6) orthogonally knitted porous scaffold.
Figure 10B:
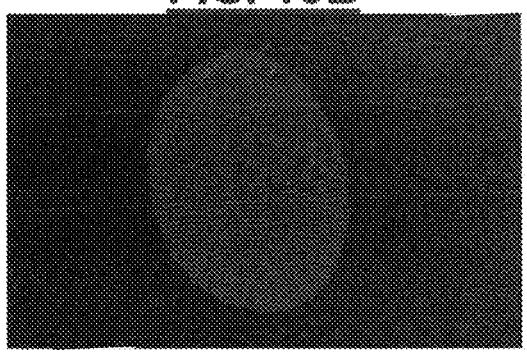
Figure 10C:
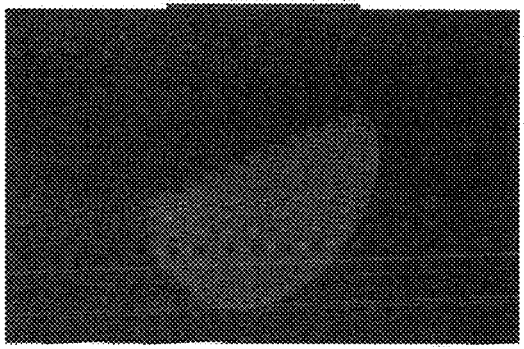
Figure 10D:
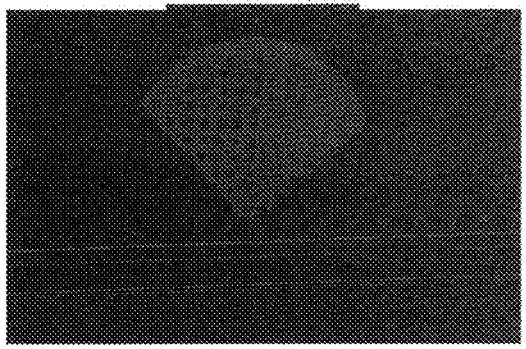

As also set forth above, the porosity of scaffolds is an important feature, as it is related to scaffold mechanical properties and degradation as well as cell attachment, growth and differentiation of the scaffold. FIG. 3A-C show the μ-CT reconstruction slices from 3D scanning using the same testing conditions between samples. The radiopacity results show the same trend as seen using polymer films. With decreasing iodine content, reduction in contrast is observed. From poly(1-PHE-6) (FIG. 3A) to poly(1-IPHE-6)$_{0.44}$-co-poly(1-PHE-6)$_{0.56}$ (FIG. 3C), the intensity of polymers under μ-CT increases with increasing iodine content. For poly(1-PHE-6) scaffold, it is difficult to see the inside structures (FIG. 3A). The copolymer scaffold results show the presence of regular square pores with sizes ranging from 250 μm-400 μm. The porosity of poly(1-PHE-6) (FIG. 3A), poly(1-IPHE-6)$_{0.24}$-co poly(1-PHE-6)$_{0.76}$ (FIG. 3B) and poly(1-IPHE-6)$_{0.44}$-co-poly(1-PHE-6)$_{0.55}$ (FIG. 3C) scaffolds were calculated to be (90±1.6)%, (85±0.4)% and (88±0.5)%, respectively. The theoretical porosity for the scaffolds was 85.6%. The porosity of poly(1-PHE-6) (FIG. 3A) that was calculated to be (90±1.6)% is not reliable since the radio contrast is too low to be accurately calculated, even though exposure time was increased to 70 ms and the voltage was decreased to 40 kV to obtain higher radio contrast for calculation. The fabrication method for the scaffolds was consistent for all three materials, so the porosity difference may be due to some material property, such as brittleness. 3D reconstruction images of scaffolds are shown in the supporting information.

The compression moduli data are summarized in Table 3. For all scaffolds, the compression moduli in the wet state are lower than those in the dry state due to water penetration in the scaffolds. In both dry and wet states, the compression modulus has the same trend: the poly(1-IPHE-6)$_{0.24}$-co-poly(1-PHE-6)$_{0.76}$ scaffold has the highest compression modulus and the poly(1-IPHE-6)$_{0.44}$-co-poly(1-PHE-6)$_{0.56}$ has the lowest. In this test, the compression modulus is mainly related to both inherent material properties and to the physical structure of the scaffolds through this empirical relationship:

$$E = E_0 e^{-bP} \quad (5)$$

where $E_0$ is the elastic modulus of the bulk material, P the porosity and b related to the microstructure.

Poly(1-PHE-6) scaffolds easily crumbled following salt-leaching due to their brittle nature. They do not maintain their original shape after 4 days in PBS, while iodinated copolymers maintain structural integrity after PBS soaking. Structural defects in poly(1-PHE-6) scaffolds caused an increase in porosity, hence a decrease in the compressive modulus. For iodinated copolymers, poly(1-IPHE-6)$_{0.24}$-co-poly(1-PHE-6)$_{0.76}$ had a superior modulus to poly(1-IPHE-6)$_{0.44}$-co-poly(1-PHE-6)$_{0.56}$. This higher compressive modulus is likely related to the higher elastic modulus detected in bulk poly(1-IPHE-6)$_{0.24}$-co-poly(1-PHE-6)$_{0.76}$ compared to that of poly(1-IPHE-6)$_{0.44}$-co-poly(1-PHE-6)$_{0.55}$.

TABLE 3

Compression modulus of PEU porous scaffolds

| Sample | Porosity (%) | Dry (MPa) | Wet (MPa) |
|---|---|---|---|
| Poly(1-PHE-6) | (90 ± 1.6)% | 2.15 ± 0.17 | 0.27 ± 0.04 |
| Poly(1-IPHE-6)$_{0.24}$-co-poly(1-PHE-6)$_{0.76}$ | (85 ± 0.4)% | 5.03 ± 0.80 | 0.79 ± 0.08 |
| Poly(1-IPHE-6)$_{0.44}$-co-poly(1-PHE-6)$_{0.56}$ | (88 ± 0.5)% | 1.19 ± 0.04 | 0.23 ± 0.05 |

Cell viability and spreading were also evaluated for these PEU polymers. FIG. 16 show the results of cell viability assays using MC3T3 cells on PEU films with different iodine content. From the representative pictures, it is evident that living cells predominate and cells are distributed uniformly on the films. The viability of cells on poly(1-PHE-6), poly(1-IPHE-6)$_{0.24}$-co-poly(1-PHE-6)$_{0.76}$) and poly(1-IPHE-6)$_{0.44}$-co-poly(1-PHE-6)$_{0.56}$) is (81.2±11.5)%, (76.8±5.1)% and (81.3±4.6)%, respectively (See FIG. 16). The observation of about 20% cell death is presumed due to cell seeding and handling. The radiopaque PEUs of the present invention are non-toxic to cells as can be seen by cell staining images showing cell actin staining. The calculated aspect ratio (See, FIG. 17) and cell area (See, FIG. 18) are similar for cells seeded on all films, even with different iodine content. This indicates that there is no significant difference in the effect of iodine content on cell activity.

As set forth herein above, a compositional series of radiopaque PEUs were synthesized from bis-L-phenylalanine-1,6-hexanediol-diester and bis-4-I-L-phenylalanine-1,6-hexanediol-diester monomers. The polymer compositions were characterized by $^1$H-NMR and FT-IR. The data illustrates that iodine can be intrinsically and controllably incorporated into PEUs based on feed ratio with varied content. Iodinated PEUs showed higher glass transition temperatures, thermal stability and radiopacity with a limited decrease in elastic modulus. The radiopacity of 500 μm poly(1-IPHE-6) film is comparable to that of a reference aluminum film with a thickness of 1 mm. Importantly, poly(1-IPHE-6)$_{0.24}$-co-poly(1-PHE-6)$_{0.76}$ and poly(1-IPHE-6)$_{0.44}$-co-poly(1-PHE-6)$_{0.55}$ are ductile. It is unusual for a material to have relatively high modulus and also ductility. This ductility enables polymer scaffolds to maintain their original shape, which explains why the poly(1-IPHE-6)$_{0.24}$-co-poly(1-PHE-6)$_{0.76}$ scaffold has the highest compression modulus. In addition to radiopacity, the modulus and ductility of iodinated PEUs can also be selectively tuned by variation of the iodine incorporation. Cell viability and spreading assays demonstrate iodinated PEUs are non-toxic. It is envisioned that these materials will find widespread application in a number of tissue engineering applications where degradation and contrast are required.

In light of the foregoing, it should be appreciated that the present invention significantly advances the art by providing a radiopaque PEU polymer (and related methods) that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Unless otherwise set for the herein, the materials used were as follows. The 4-Iodo-L-phenylalanine (95+%) was purchased from VWR. L-phenylalanine, 1,6-hexanediol, p-toluene sulfonic acid monohydrate, activated carbon black, calcium hydride, sodium carbonate, triphosgene (98.00%), toluene, chloroform, 1,1,1,3,3,3-hexafluoro-2-propanol (HFIP), ethanol and N,N-dimethyl formamide (DMF) were purchased from Sigma-Aldrich or Alfa Aesar. Chloroform was dried and distilled before use. All other chemicals were used as received.

$^1$H-NMR and $^{13}$C-NMR spectra of monomers and polymers were obtained using Varian NMR Spectrophotometer (500 MHz). All chemical shifts were reported in ppm (S) with solvent resonances ($^1$H-NMR DMSO-d$_6$ 2.50 ppm; $^{13}$C-NMR DMSO-d$_6$ 39.50 ppm). Abbreviations of s, d and m were used to represent singlet, doublet and multiplet. Fourier transform infrared spectra (FT-IR) of PEUs were characterized using Excalibur Spectrometer FTS 3000. Measurements were conducted by preparing KBr pellet and recording the spectra using 64 scans with 4 cm$^{-1}$ resolution. Molecular masses of polymers were obtained from size exclusion chromatography (SEC) analysis (TOSOH HLC-8320 gel permeation chromatograph) using DMF (with 0.01 M LiBr) as eluent (flow rate 1 mL/min) at 50° C. and a refractive index detector. Thermogravimetric Analysis (TGA, TA Q500) was used to measure the thermal properties of PEUs at a heating rate of 20° C./min from room temperature to 600° C. under nitrogen atmosphere. The glass transition temperature, Tg, was determined using Differential Scanning calorimetry (DSC, TA Q200) at a scanning rate of 20° C./min from −20° C. to 200° C. for 3 cycles. The midpoint of the transition shown in the second heating cycle was used to determine Tg.

Example 1

Synthesis of di-p-toluene sulfonic acid salt of bis-L-phenylalanine-1,6-hexanediol-diester (1-PHE-6 monomer) and di-p-toluene sulfonic acid salt of bis-4-I-L-phenylalanine-1,6-hexanediol-diester (1-IPHE-6 monomer)

1-PHE-6 and 1-IPHE-6 monomers were synthesized as described previously (See e.g, Stakleff, K. S.; Lin, F.; Callahan, L. A. S.; Wade, M. B.; Esterle, A.; Miller, J.; Graham, M.; Becker, M. L. *Acta Biomater.* 2013, 9, 5132-5142, the contents of which are hereby incorporated by reference in their entirety). 1,6-hexanediol (20.00 g, 1.0 equiv., 0.17 mol), L-phenylalanine (64.32 g, 2.3 equiv., 0.39 mol), p-toluene sulfonic acid monohydrate (77.29 g, 2.4 equiv., 0.41 mol) and toluene (500 mL) were mixed in a 1 L one-neck round-bottomed flask using a magnetic stir bar with a dean stark trap. The system was refluxed at 110° C. for 21 h. The crude product was vacuum filtered overnight to remove toluene, decolorized by activated carbon black (4.00 g) and recrystallized from boiling water 4 times to yield 105.50 g (yield 82.4%). $^1$H-NMR (500 MHz, DMSO-$d_6$): 1.06 (m, 4H), 1.38 (m, 4H), 2.27 (s, 6H), 2.48 (m, DMSO), 2.97-3.15 (m, 4H), 3.29 (s, $H_2O$), 3.98-4.03 (m, 4H), 4.25-4.28 (m, 2H), 7.09-7.11 (d, 4H), 7.20-7.30 (m, 10H), 7.41-7.49 (d, 4H), 8.36 (s, 6H). $^{13}$C-NMR (500 MHz, DMSO-$d_6$): 20.84, 24.72, 27.65, 36.22, 38.67-39.78 (DMSO-$d_6$), 53.36, 65.48, 125.56, 127.26, 128.24, 128.58, 129.34, 134.73, 138.14, 145.03, 169.08.

The synthesis of 1-IPHE-6 monomer was performed using the same method, but alcohol was added to the water (1:1) to increase solubility for recrystallization. 1,6-hexanediol (17.63 g, 1.00 equiv., 0.15 mol), 4-I-L-phenylalanine (100.00 g, 2.3 equiv., 0.34 mol), p-toluene sulfonic acid monohydrate (68.13 g, 2.4 equiv., 0.36 mol) and toluene (1000 mL) were mixed in a 2 L one-neck round-bottomed flask using a magnetic stir bar with a dean stark trap. The system was refluxed at 110° C. for 21 h. The crude product was vacuum filtered overnight to remove toluene, and was recrystallized from mixture solvent of alcohol and water (1:1) 4 times to yield 111.40 g (yield 74.0%). $^1$H-NMR (500 MHz, DMSO-$d_6$): 1.05 (m, 4H) 1.39 (m, 4H) 2.27 (s, 6H) 2.48 (m, DMSO) 2.92-3.11 (m, 4H) 3.32 (s, $H_2O$) 4.02-4.03 (m, 4H) 4.26-4.30 (m, 2H), 7.02-7.69 (m, 16H). $^{13}$C-NMR (500 MHz, DMSO-$d_6$): 21.25, 25.24, 28.15, 36.05, 39.16-40.83 (DMSO-$d_6$), 53.42, 66.03, 93.84 (C-I), 125.95, 128.58, 132.18, 134.94, 137.75, 138.33, 145.73, 169.37.

Example 2

Synthesis of bis-L-phenylalanine-1,6-hexanediol-diester PEU (poly(1-PHE-6)), bis-4-I-L-phenylalanine-1,6-hexanediol-diester PEU (poly(1-IPHE-6)), co-polymers of 1-IPHE-6 monomer and 1-PHE-6 monomer (1:4 molar ratio, poly(1-IPHE-6)$_{0.24}$-co-poly(1-PHE-6)$_{0.76}$) and co-poly(ester urea) of 1-IPHE-6 monomer and 1-PHE-6 monomer (3:4 molar ratio, poly(1-IPHE-6)$_{0.4}$-co-poly(1-PHE-N$_{0.56}$)

Di-p-toluene sulfonic acid salt of bis-L-phenylalanine-1,6-hexanediol-diester (1-PHE-6 monomer) (30.00 g, 1.0 equiv., 0.04 mol), sodium carbonate (8.83 g, 2.1 equiv., 0.083 mol) and 400 mL distilled water were added to a 3 L 3-neck round bottom flask. The contents were mechanically stirred at 35° C. until the mixture was dissolved. The 35° C. water bath was then replaced with an ice bath. When the reaction temperature reached 0° C., additional sodium carbonate (4.42 g, 1.05 equiv., 0.042 mol) was dissolved in 150 mL distilled water and added to the flask. Triphosgene (4.21 g, 0.35 equiv., 0.014 mol, 98%), dissolved in distilled chloroform (100 mL), was added to the flask quickly. After 30 minutes, additional triphosgene (1.00 g, 0.08 equiv., 0.003 mol, 98%), dissolved in distilled chloroform (30 mL), was added to the flask dropwise for 2 h. The crude product was transferred to a separatory funnel and precipitated into boiling water dropwise to obtain polymer 15.99 g (yield 92.0%). $^1$H-NMR (500 MHz, DMSO-$d_6$): 1.15 (m, 4H) 1.43 (m, 4H) 2.49 (DMSO) 2.85-2.94 (m, 4H) 3.29 (s, $H_2O$), 3.94 (m, 4H) 4.35-4.39 (m, 2H) 6.47-6.48 (m, 2H) 7.13-7.26 (m, 10H). $^{13}$C-NMR (500 MHz, DMSO-$d_6$): 25.32, 28.35, 38.15, 39.52-40.53 (DMSO), 54.50, 64.72, 126.97, 128.65, 129.59, 137.33, 157.09, 172.70.

The same procedure was used to synthesize the other three polymers, except for the use of different amounts of the monomers in copolymerization.

For poly(1-IPHE-6), di-p-toluene sulfonic acid salt of bis-4-I-L-phenylalanine-1,6-hexanediol-diester (1-IPHE-6 monomer) (8.00 g, 1.0 equiv., 7.94 mmol), sodium carbonate (1.77 g, 2.1 equiv., 16.70 mmol) and 133 mL distilled water were added to a 1 L 3-neck round bottom flask. The contents were mechanically stirred at 35° C. until the mixture was dissolved. The 35° C. water bath was then replaced with an ice bath. When the reaction temperature reached 0° C., additional sodium carbonate (0.88 g, 1.05 equiv., 8.33 mmol) was dissolved in 50 mL distilled water and added to the flask. Triphosgene (0.84 g, 0.35 equiv., 2.83 mmol, 98%), dissolved in distilled chloroform (33 mL), was added to the flask quickly. After 30 minutes, additional triphosgene (0.20 g, 0.08 equiv., 0.67 mmol, 98%), dissolved in distilled chloroform (10 mL), was added to the flask dropwise for 2 h. The crude product was transferred to a separatory funnel and precipitated into boiling water dropwise to obtain polymer 4.85 g (yield 88.6%). $^1$H-NMR (500 MHz, DMSO-$d_6$): 1.17 (m, 4H) 1.44 (m, 4H) 2.49 (DMSO) 2.81-2.90 (m, 4H) 3.29 (s, $H_2O$), 3.94-3.97 (m, 4H) 4.33-4.37 (m, 2H) 6.43-6.45 (m, 2H) 6.93-6.95 (m, 4H) 7.58-7.60 (m, 4H). $^{13}$C-NMR (500 MHz, DMSO-$d_6$): 25.38, 28.39, 37.58, 39.53-40.63 (DMSO), 54.17, 64.85, 92.89, 132.04, 137.39, 156.98, 172.48.

For copolymer of 1-IPHE-6 monomer and 1-PHE-6 monomer at 1:4 in molar ratio (poly(1-IPHE-6)$_{0.24}$-co-poly(1-PHE-6)$_{0.76}$), di-p-toluene sulfonic acid salt of bis-4-I-L-phenylalanine-1,6-hexanediol-diester (1-IPHE-6 monomer) (3.00 g, 1.0 equiv., 2.98 mmol), di-p-toluene sulfonic acid salt of bis-L-phenylalanine-1,6-hexanediol-diester (1-PHE-6 monomer) (9.00 g, 1.0 equiv., 11.90 mmol), sodium carbonate (3.31 g, 2.1 equiv., 31.23 mmol) and 133 mL distilled water were added to a 1 L 3-neck round bottom flask. The contents were mechanically stirred at 35° C. until the mixture was dissolved. The 35° C. water bath was then replaced with an ice bath. When the reaction temperature reached 0° C., additional sodium carbonate (1.66 g, 1.05 equiv., 15.66 mmol) was dissolved in 50 mL distilled water and added to the flask. Triphosgene (1.58 g, 0.35 equiv., 5.32 mmol, 98%), dissolved in distilled chloroform (33 mL), was added to the flask quickly. After 30 minutes, additional triphosgene (0.38 g, 0.08 equiv., 1.27 mmol, 98%), dissolved in distilled chloroform (10 mL), was added to the flask dropwise for 2 h. The crude product was transferred to a separatory funnel and precipitated into boiling water dropwise to obtain polymer 6.83 g (yield 94.0%). $^1$H-NMR (500 MHz, DMSO-$d_6$): 1.16 (m, 4H) 1.43 (m, 4H) 2.49 (DMSO) 2.81-2.94 (m, 4H) 3.29 (s, $H_2O$), 3.93-3.95 (m, 4H) 4.35-4.39 (m, 2H) 6.43-6.48 (m, 2H) 6.94-7.60 (m, 9.52H). $^{13}$C-NMR (500 MHz, DMSO-$d_6$): 25.32, 28.35, 38.16, 39.52-40.53 (DMSO), 54.50, 64.72, 92.86, 126.97, 128.65, 129.59, 132.05, 137.33, 157.09, 172.70.

For copolymers of 1-IPHE-6 monomer and 1-PHE-6 monomer at 3:4 in molar ratio (poly(1-IPHE-6)$_{0.44}$-co-poly (1-PHE-6)$_{0.56}$), di-p-toluene sulfonic acid salt of bis-4-I-L-phenylalanine-1,6-hexanediol-diester (1-IPHE-6 monomer) (6.00 g, 1.0 equiv., 5.95 mmol), di-p-toluene sulfonic acid salt of bis-L-phenylalanine-1,6-hexanediol-diester (1-PHE-6 monomer) (6.00 g, 1.0 equiv., 7.94 mmol), sodium carbonate (3.09 g, 2.1 equiv., 29.15 mmol) and 133 mL distilled water were added to a 1 L 3-neck round bottom flask. The contents were mechanically stirred at 35° C. until the mixture was dissolved. The 35° C. water bath was then replaced with an ice bath. When the reaction temperature reached 0° C., additional sodium carbonate (1.55 g, 1.05 equiv., 14.62 mmol) was dissolved in 50 mL distilled water and added to the flask. Triphosgene (1.47 g, 0.35 equiv., 4.96 mmol, 98%), dissolved in distilled chloroform (33 mL), was added to the flask quickly. After 30 minutes, additional triphosgene (0.35 g, 0.08 equiv., 1.18 mmol, 98%), dissolved in distilled chloroform (10 mL), was added to the flask dropwise for 2 h. The crude product was transferred to a separatory funnel and precipitated into boiling water dropwise to obtain polymer 7.02 g (yield 92.6%). $^1$H-NMR (500 MHz, DMSO-$d_6$): 1.16 (m, 4H) 1.43 (m, 4H) 2.49 (DMSO) 2.81-2.93 (m, 4H) 3.28 (s, $H_2O$), 3.94-3.95 (m, 4H) 4.32-4.39 (m, 2H) 6.43-6.48 (m, 2H) 6.93-7.60 (m, 9.12H). $^{13}$C-NMR (500 MHz, DMSO-$d_6$): 25.32, 28.36, 38.15, 39.53-40.53 (DMSO), 54.49, 64.73, 92.87, 126.97, 128.65, 129.59, 132.04, 137.39, 157.04, 172.69.

Example 3

PEU Films and 3D Porous Scaffold Preparation and Characterization

Films with two sizes (25 mm*5 mm*0.5 mm film and 10 mm*2 mm*0.2 mm) were prepared by vacuum compression molding as published[45] (temperature 150° C., TMP Technical Machine Products Corp). 3D porous scaffolds were fabricated as previously described[51] by casting polymer solution (2 g polymer in 5 mL DMF) into sieved salt (weight: 22 g, size: 250 μm-400 μm and theory porosity: 85.6%[52]). DMF was removed by vacuum drying at 65° C. for 3 days and the salt was leached in deionized water for 3 days. The obtained porous scaffolds were dried and cut into 7 mm*7 mm*7 mm for characterization (6 samples for each scaffold). In order to prepare wet samples, dry scaffolds were soaked in PBS buffer for 4 days (3 samples for each polymer in each condition).

The mechanical properties of the films were measured using Dynamic Mechanical Analysis (DMA Q800) with a strain rate of 2.5%/min at room temperature. The sample sizes used were 10 mm, 2 mm, and 0.2 mm (3 samples for each polymer). The slope from the linear region of each stress-strain curve was calculated as the elastic modulus. The compression modulus of 3D scaffolds was obtained using Instron (Instron 5567 Universal Testing Machine, compression mode) with a compression speed of 0.5 mm/min for 4 min at room temperature. The compression modulus, the slope of the linear region in the compression stress-strain curve, in both dry and wet states was analyzed.

Radiopacity of the polymers was characterized nondestructively using X-ray micro-computed tomography (μ-CT). In μ-CT (Micro-CT, Skyscan 1172) projection, 25 mm*5 mm*0.5 mm films were used. The following parameters were adopted when using μ-CT: 100 kV voltage, medium camera, 0.5 mm Al filter and 9.9 μm resolution. An aluminum wedge (0.5-2.5 mm in 0.5 mm step) was used as the contrast standard reference.[50] The porosity of scaffolds was also characterized nondestructively by μ-CT. 3D scanning of scaffolds was carried out under the following parameters: 60 kV voltage, large camera, no filter, 30 ms camera exposure preset time and 18.4 μm resolution. In order to have sufficient contrast for PEU scaffolds, the following parameters were used: 40 kV voltage, large camera, no filter, 70 ms camera exposure preset time and 15.0 μm resolution. In this test, projections from different angles were obtained and reconstructed by the NRecon program and analyzed by the CTAn program.

Example 4

In Vitro Cell Viability and Spreading Characterization

PEU films were prepared on 12 mm diameter cover glass by spin coating of 5 wt % PEU solution (dosslved in HFIP), vacuum dried at 80° C. overnight and carefully moved to wells of a 24-well plate using tweezers. All samples were sterilized in 70% ethanol for 20 minutes, rinsed once in PBS to remove residual ethanol, and then submerged in 1 mL media prior to seeding. Cells were rinsed with PBS and detached from the bottom of the flask using 0.05% Trypsin/EDTA at 37° C., 95% humidity, 5% $CO_2$ for 5 minutes. Detached cells were then collected into a conical tube containing equal parts media to trypsin. Cells were centrifuged into a pellet at 3,000 rpm, 4° C. for 1 minute. The media/trypsin was aspirated and cells were re-suspended in fresh media. Then cells were counted using a hemacytometer with trypan blue exclusion. Cells were seeded at a density of 25 cells/mm$^2$ in 100 μL aliquots per sample by dripping into the center of sample wells containing 1 mL of media. The well plate was agitated to ensure even dispersion of cells over samples prior to incubation at 37° C., 95% humidity, 5% $CO_2$ for 24 hours.

Cell viability was assessed using a LIVE/DEAD™ viability assay (Life Technologies). 5 μl of calcein AM (4 mM) and 104 of ethidium homodimer (2 mM) were added to 10 mL of DPBS as a working solution. Media was aspirated from all samples, samples were rinsed once in DPBS, and then 0.5 mL of the working solution was added to each well. Samples were incubated for 10 minutes at 37° C. before imaging at 4× magnification using CellSENS™ imaging software with an Olympus microscope equipped with a Hamamatsu Orca R2 CCD camera and a filter cube containing FITC and TRITC fluorescence filters. Images were analyzed for live/dead cell counts using Image J (NIH) software with a cell counter plugin. Cells stained green were counted as live and cells that stained red were counted as dead. Live and dead cell counts for all images per sample were totaled to calculate % viability for each sample. (See FIG. 17)

After 24 hours of incubation, cells were fixed first by adding 0.6 mL of 3.7% paraformaldehyde in PBS to 0.4 mL media in each well for 10 minutes, and then in 1 mL of 3.7% paraformaldehyde in PBS for 5 minutes at 37° C. Cells were then permeabilized using 0.5% tritonX-100 in cytoskeletal stabilization (CS) buffer for 9 minutes at 37° C. Samples were rinsed three times, 5 minutes each time, in CS buffer at room temperature. Aldehyde autofluorescence was then quenched using 0.1% sodium borohydride in CS buffer for 10 minutes at room temperature. Non-specific staining was blocked using 5% donkey serum in PBS for 20 minutes at 37° C. Samples were then rinsed three times, 5 minutes each time, in CS buffer at room temperature. Cells were stained with 6 μM DAPI (Life Technologies) in CS Buffer for 10 minutes at 37° C. Cells were then stained to observe cytoskeletal actin using rhodamine-phalloidin (Life Technologies) (6.6 μM diluted 1:40 in 1% donkey serum) for 1 h at 37° C. After staining cells were rinsed three times in 1% donkey serum and two times in PBS with no wait. Samples were imaged immediately using CelLSENS® imaging software with an Olympus microscope equipped with a Hamamatsu Orca R2 CCD camera and a filter cube containing DAPI and TRITC fluorescence filters. Images were analyzed for cell aspect ratio and cell area using Image J (NIH) software. Cell aspect ratio was quantified using the cells greatest length divided by the diameter of the cell across the center of the nucleus. Twenty cells per image were used to calculate average cell spreading as well as cell area for each sample (n=3).

Example 5

Determination of Radiopacity

Radiopacity was characterized nondestructively by μ-CT with an aluminum wedge (0.5-2.5 mm in 0.5 mm step) as a reference standard. Aluminum is radiopaque and the radio contrast increases linearly with thickness. Accordingly, the radio contrast of PEU films was compared to the standard aluminum wedge reference to qualitatively determine radiopacity of the samples. For example, the poly(1-IPHE-6) film has comparable radio contrast to that of the aluminum reference with a thickness of 1 mm and poly(1-IPHE-6)$_{0.44}$-co-poly(1-PHE-6)$_{0.56}$ film has comparable radio contrast as that of the aluminum reference with a thickness of 0.5 mm. In the shadow projection, darker image indicates higher radiopacity and better contrast. In the reconstruction images, the image is reversed and the brighter zone indicates higher radiopacity. (See e.g. FIGS. 2, 3A-C, 4A-C, 5, 6, 7A-D, 8, 9A-D, 10A-D, and 11A-D)

Example 6

In Scaffold Fabrication by 3D Printing

To obtain polymer filament with no air bobble, poly(1-PHE-6) and poly(1-IPHE-6)$_{0.12}$-co-poly(1-PHE-6)$_{0.88}$ films (150 mm*150 mm*1.5 mm) were first prepared by vacuum compression molding at 160° C. and 150° C., respectively (TMP Technical Machine Products Corp). Then polymer film was cut into pieces and fed into capillary rheometer (Bohlin (Malvern) RH7 advanced Capillary Rheometer) equipped with 2.0 mm die and a take up roller. The extrusion temperature was 170° C. for poly(1-PHE-6) and 150° C. for poly(1-IPHE-6)$_{0.12}$-co-poly(1-PHE-6)$_{0.88}$. The filament extrusion rate was 20 mm/min and take up rate was 5 rpm/min.

PEU filament prepared by capillary rheometer extrusion was used as feeding material in 3D printing (CartesioW equipped with 0.25 mm nozzle). The printing temperature was 170° C. for poly(1-PHE-6) and 160° C. for poly(1-IPHE-6)$_{0.12}$-co-poly(1-PHE-6)$_{0.88}$. Scaffolds with tubular structure (2.2 mm inner diameter, 1.0 mm wall thickness, 100% fill density and 2 mm/s printing speed) and orthogonally knitted porous structure (10 mm diameter, 2.5 mm thickness, 50% fill density and 40 mm/s printing speed) were prepared as designed (Google SketchUp 8). For all the scaffolds, the printed fiber was 0.25 mm diameter and layer height was 0.15 mm. See FIGS. 4A-C, 8, 9A-D, 10A-D, and 11A-D.

Example 7

Micro-CT 3D Scanning of Scaffolds

Radiopacity and scaffold structure were characterized by X-ray micro-computed tomography (μ-CT). 3D scanning of tubular scaffolds was carried out under the following parameters: 60 kV voltage, medium camera, no filter, 30 ms camera exposure preset time and 8.0 μm resolution. And for the orthogonally knitted porous structure, the scanning conditions were the same except using 60 kV voltage. See FIGS. 4A-C, 8, 9A-D, 10A-D, and 11A-D.

What is claimed is:

1. A radiopaque poly(ester urea) polymer comprising two or more amino acid-based monomer segments containing at least one amino acid residue functionalized to include a radiopaque atom.

2. The radiopaque poly(ester urea) polymer of claim 1, wherein said radiopaque atom is selected from the group consisting of iodine, boron, and combinations thereof.

3. The radiopaque poly(ester urea) polymer of claim 1, wherein said radiopaque atom is iodine.

4. The radiopaque poly(ester urea) polymer of claim 1, wherein said amino acid residue is an L-phenylalanine residue.

5. The radiopaque poly(ester urea) polymer of claim 1 having the formula:

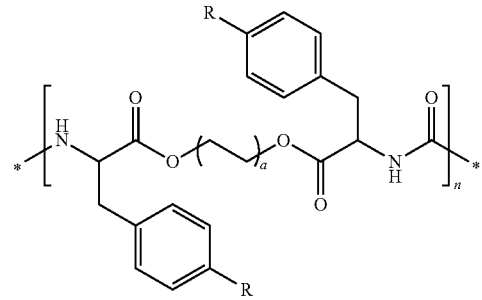

wherein R is I or H with the proviso that at least one R in said radiopaque poly(ester urea) polymer is I, a is an integer from 2 to 20, and n is an integer from 10 to 1000.

6. A radiopaque poly(ester urea) polymer comprising:
one or more first amino acid-based monomer segments, wherein said first amino acid-based monomer segments further comprise two or more iodine functionalized amino acid residues separated by from about 2 to about 20 carbon atoms; and
one or more second amino acid-based monomer segments, wherein said second amino acid-based monomer segments further comprise two or more amino acid residues separated by from about 2 to about 20 carbon atoms.

7. The radiopaque poly(ester urea) polymer of claim 6 wherein said two or more iodine functionalized amino acid residues are iodine functionalized L-phenylalanine residues.

8. The radiopaque poly(ester urea) polymer of claim 6 wherein said two or more amino acid residues of said second amino acid-based monomer segments are residues of alanine (ala-A), arginine (arg-R), asparagine (asn-N), aspartic acid (asp-D), cysteine (cys-C), glutamine (gln-Q), glutamic acid (glu-E), glycine (gly-G), histidine (his-H), isoleucine (ile-I), leucine (leu-L), lysine (lys-K), methionine (met-M), phenylalanine (phe-F), serine (ser-S), threonine (thr-T), tryptophan (trp-W), tyrosine (tyr-Y), or valine (val-V).

9. The radiopaque poly(ester urea) polymer of claim 6 wherein said two or more iodine functionalized amino acid residues comprise 4-iodo-L-phenylalanine.

10. The radiopaque poly(ester urea) polymer of claim 6 wherein said one or more first amino acid-based monomer segments comprise the residue of bis-4-I-L-phenylalanine-1,6-hexanediol-diester.

11. The radiopaque poly(ester urea) polymer of claim 6 wherein said two or more iodine functionalized amino acid residues are separated by from about 2 to about 20 carbon atoms.

12. The radiopaque poly(ester urea) polymer of claim 6 wherein said two or more iodine functionalized amino acid residues are separated by six carbon atoms.

13. The radiopaque poly(ester urea) polymer of claim 6 wherein said two or more amino acid residues of said second amino acid-based monomer segments are separated by from about 2 to about 20 carbon atoms.

14. The radiopaque poly(ester urea) polymer of claim 6 wherein two or more amino acid residues of said second amino acid-based monomer segments are separated by six carbon atoms.

15. The radiopaque poly(ester urea) polymer of claim 6 having the formula:

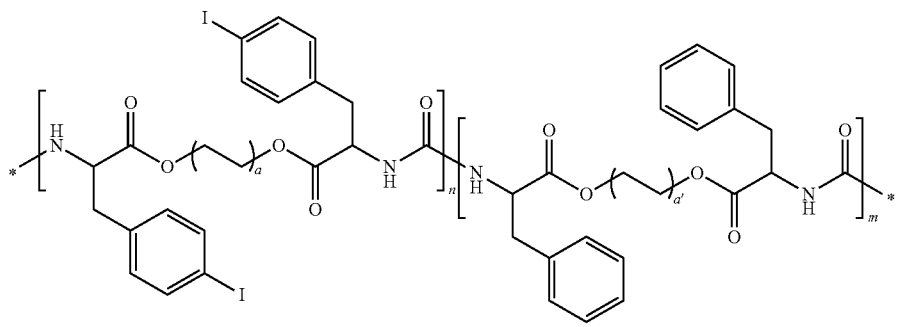

wherein a and a' are each integers from 2 to 20; n is a mole percentage from about 1 to about 100; and m is a mole percentage from about 0 to about 99.

16. The radiopaque poly(ester urea) polymer of claim 6 wherein said first amino acid-based monomer segments comprise from 1% to 100% of said radiopaque poly(ester urea) polymer.

17. A method for making a radiopaque poly(ester urea) polymer comprising:
A. dissolving L-phenylalanine, a linear or branched polyol having from about 2 to about 60 carbon atoms, and an acid in a suitable solvent;
B. refluxing the solution of Step A to form the acid salt of a first amino acid-based monomer having two or more L-phenylalanine residues separated by from about 2 to about 20 carbon atoms;
C. dissolving L-phenylalanine functionalized with a radiopaque moiety, a linear or branched polyol having from 2 to about 60 carbon atoms, and an acid in a suitable solvent;
D. refluxing the mixture of Step C to form the acid salt of a second amino acid-based monomer having two or more iodine functionalized L-phenylalanine residues separated by from about 2 to about 20 carbon atoms;
E. dissolving the acid salt of said first amino acid-based monomer, the acid salt of said second amino acid based monomer, and an organic water soluble base in distilled water;
F. cooling the mixture of Step E to a temperature of from about −10° C. to about 2° C.;
G. dissolving an additional quantity of an organic water soluble base in distilled water and adding it to the mixture of Step F;
H. dissolving a first fraction of triphosgene in distilled chloroform and adding it to the mixture of Step G; and
I. dissolving a second fraction of triphosgene in distilled chloroform and adding it dropwise to the mixture of Step H over a period of from about 5 minutes to about 72 hours to form a radiopaque poly(ester urea) polymer.

18. The method for making a radiopaque poly(ester urea) polymer of claim 17 wherein said acid is p-toluene sulfonic acid monohydrate.

19. The method for making a radiopaque poly(ester urea) polymer of claim 17 wherein said organic water soluble base is sodium carbonate.

20. The method for making a radiopaque poly(ester urea) polymer of claim 17 wherein the radiopaque moiety is iodine.

21. The method for making a radiopaque poly(ester urea) polymer of claim 17 further comprising:
J. collecting and purifying said radiopaque poly(ester urea) polymer of Step I by transferring the mixture of step I to a separatory funnel, thereby forming a aqueous layer and a organic layer containing the radiopaque poly(ester urea) polymer;
K. adding said organic layer dropwise into boiling water thereby causing the radiopaque poly(ester urea) polymer to precipitate;
L. collecting the radiopaque poly(ester urea) polymer by filtration, and drying.

22. The method for making a radiopaque poly(ester urea) polymer of claim 17 wherein the molar ratio of the acid salt of said first amino acid-based monomer to the acid salt of said second amino acid based monomer is from about 1% to about 99%.

23. The method for making a radiopaque poly(ester urea) polymer of claim 17 wherein the molar ratio of the acid salt of said first amino acid-based monomer to the acid salt of said second amino acid based monomer is 1% to 99%.

24. A medical device comprising the radiopaque poly(ester urea) polymer of claim 1.

25. The medical device of claim 24, wherein said medical device comprises a tissue scaffold, 3D printed material, drug eluting scaffold, thin film or coating.

26. The medical device of claim 24, wherein said medical device as formed by a process selected from the group consisting of extrusion, three-dimensional (3D) printing, injection molding, melt spinning, and combinations thereof.

* * * * *